US009272038B2

(12) United States Patent
McCarron et al.

(10) Patent No.: US 9,272,038 B2
(45) Date of Patent: Mar. 1, 2016

(54) WOUND CARE FORMULATION

(75) Inventors: Paul Anthony McCarron, Newtownabbey (GB); Mark Godfrey Jenkins, Belfast (GB); Ryan Gerald Loughlin, Banbridge (GB)

(73) Assignee: Innovation Ulster Limited, Londonderry (GB)

( * ) Notice: Subject to any disclaimer, the term of this patent is extended or adjusted under 35 U.S.C. 154(b) by 671 days.

(21) Appl. No.: 12/733,776

(22) PCT Filed: Sep. 16, 2008

(86) PCT No.: PCT/GB2008/050828
§ 371 (c)(1),
(2), (4) Date: Jul. 21, 2010

(87) PCT Pub. No.: WO2009/037500
PCT Pub. Date: Mar. 26, 2009

(65) Prior Publication Data
US 2010/0286205 A1 Nov. 11, 2010

(30) Foreign Application Priority Data
Sep. 21, 2007 (GB) .................................. 0718435.1

(51) Int. Cl.
| | |
|---|---|
| A61K 47/32 | (2006.01) |
| A61K 8/00 | (2006.01) |
| A61K 8/81 | (2006.01) |
| A61K 31/16 | (2006.01) |
| A61K 31/445 | (2006.01) |
| A61K 31/351 | (2006.01) |
| C14C 1/06 | (2006.01) |
| A61P 17/02 | (2006.01) |
| A61K 47/02 | (2006.01) |
| A61K 9/06 | (2006.01) |
| A61L 26/00 | (2006.01) |

(52) U.S. Cl.
CPC . *A61K 47/02* (2013.01); *A61K 9/06* (2013.01); *A61K 47/32* (2013.01); *A61L 26/008* (2013.01); *A61L 26/0014* (2013.01); *A61L 26/0066* (2013.01); *A61L 2300/402* (2013.01); *A61L 2300/602* (2013.01)

(58) Field of Classification Search
None
See application file for complete search history.

(56) References Cited

U.S. PATENT DOCUMENTS

| | | | |
|---|---|---|---|
| 5,505,953 A | 4/1996 | Chowhan | 424/427 |
| 6,444,199 B1 | 9/2002 | Renn | 424/78.26 |
| 2002/0122771 A1 | 9/2002 | Holland et al. | 424/43 |
| 2004/0166131 A1 | 8/2004 | Pinna et al. | 424/401 |
| 2005/0214376 A1* | 9/2005 | Faure et al. | 424/486 |
| 2007/0059274 A1 | 3/2007 | Asgharian et al. | 424/78.18 |

FOREIGN PATENT DOCUMENTS

CN 1093897 10/1994

OTHER PUBLICATIONS

International Search Report for International Application No. PCT/GB2008/050828, pp. 1-3.
Kurokawa H, Shibayama M, Ishimaru T, Nomura S, Wu WI. Phase-behavior and sol-gel transition of poly(vinyl alcohol) borate complex in aqueous-solution. Polymer. 1992; 33(10):2182-2188.
Shibayama M, Adachi M, Ikkai F, Kurokawa H, Sakurai S, Nomura S. Gelation of poly(vinyl alcohol) vanadate aqueous-solutions. Macromolecules. 1993; 26(4):623-627.
Tsujimoto M, Shibayama M. Dynamic light scattering study on reentrant sol-gel transition of poly(vinyl alcohol)-congo red complex in aqueous media. Macromolecules. 2002; 35(4):1342-1347.
Eliseev AA, Lukashin AV, Vertegel AA, Heifets LI, Zhirov AI, Tretyakov YD. Complexes of cu(II) with polyvinyl alcohol as precursors for the preparation of CuO/SiO2 nanocomposites. Materials Research Innovations. 2000; 3(5):308-312.
Bowcher TL, Dawber JG. C-13 and B-11 nuclear magnetic-resonance study of the reaction of Poly(vinyl-alcohol) with the tetrandroxyborate ion. Polymer Communications. 1989; 30(7):215-217.
Dawber JG, Green SIE. An B-11 nuclear-magnetic-resonance study of the reaction of the tetrahydroxyborate ion with polyhydroxy compounds. Journal of the Chemical Society—Faraday Transactions i. 1986; 82:3407-3413.
Lin HL, Yu TL, Cheng CH. Reentrant behavior of poly(vinyl-alcohol)-borax semidilute aqueous solutions. Colloid and Polymer Science. 2000; 278(3):187-194.
Lin HL, Liu WH, Liu YF, Cheng CH. Complexation equilibrium constants of poly(vinyl-alcohol)-borax dilute aqueous solutions—consideration of electrostatic charge repulsion and free ions charge shielding effect. Journal of Polymer Research—Taiwan. 2002; 9(4):233-238.
Pezron E, Leibler L, Lafuma F. Complex-formation in polymer-ion solutions .2. poly-electrolyte effects. Macromolecules. 1989; 22(6):2656-2662.
Pezron E, Leibler L, Ricard A, Lafuma F, Audebert R. Complex-formation in polymer ion solutions .1. polymer concentration effects. Macromolecules. 1989; 22(3):1169-1174.
Pezron E, Ricard A, Lafuma F, Audebert R. Reversible gel formation induced by ion complexation .1. borax galactomannan interactions. Macromolecules. 1988; 21(4):1121-1125.
Lin HL, Liu YF, Yu TL, Liu WH, Rwei SP. Light scattering and viscoelasticity study of poly(vinyl alcohol)-borax aqueous solutions and gels. Polymer. 2005; 46(15):5541-5549.

(Continued)

*Primary Examiner* — Mina Haghighatian
*Assistant Examiner* — Erin Hirt
(74) *Attorney, Agent, or Firm* — Timothy J. Monahan; Monahan & Company, LLC

(57) ABSTRACT

A gel formulation for use in filling a wound cavity and delivering active ingredient thereto, having a pH range of 6.5 to 7.5, low bioadhesive strength and cohesive integrity and being a PVA borate gel including an active ingredient and a modulator to bind borate and/or PVA in aqueous solution through a mono-diol or di-diol formation and reduces the pH of PVA-borate hydrogels. A suitable modulator is a sugar alcohol such as mannitol and the active ingredient, a medicament suitable for topical application such as a local anaesthetic and/or an antibiotic.

10 Claims, 10 Drawing Sheets

(56) References Cited

OTHER PUBLICATIONS

Figure 1:
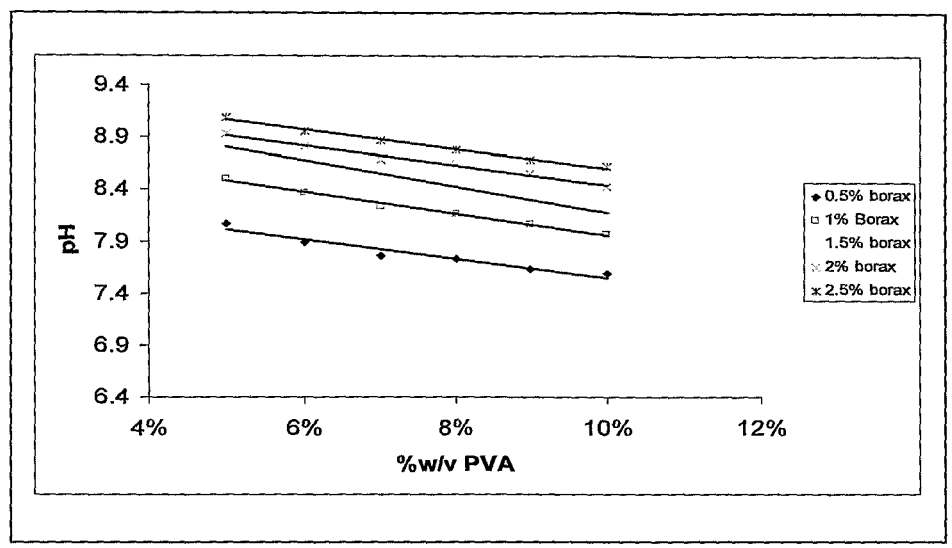

Koike A, Nemoto N, Inoue T, Osaki K. Dynamic light-scattering and dynamic viscoelasticity of poly(vinyl alcohol) in aqueous borax solutions .1. concentration-effect. Macromolecules. 1995; 28(7):2339-2344.

Nemoto N, Koike A, Osaki K. Dynamic light scattering and dynamic viscoelasticity of poly(vinyl alcohol) in aqueous borax solutions .2. polymer concentration and molecular weight effects. Macromolecules. 1996; 29(5):1445-1451.

Takada A, Nishimura P, Koike A, Nemoto N. Dynamic light scattering and dynamic viscoelasticity of poly(vinyl alcohol) in aqueous borax solutions .4. further investigation on polymer concentration and molecular weight dependencies. Macromolecules. 1998; 31(2):436-443.

Koga K, Takada A, Nemoto N. Dynamic light scattering and dynamic viscoelasticity of poly(vinyl alcohol) in aqueous borax solutions .5. temperature effects. Macromolecules. 1999; 32(26):8872-8879.

Lin HL, Liu WH, Shen KS, Yu TL, Cheng CH. Weak gel behavior of poly(vinyl alcohol)-borax aqueous solutions. Journal of Polymer Research—Taiwan. 2003; 10(3):171-179.

Ide N, Sato T, Miyamoto T, Fukuda T. Thermoreversible hydrogel of short-chain O-(2,3-dihyroxypropyl)cellulose/borax aqueous solution. Microscopic versus macroscopic properties. Macromolecules. 1998; 31(25):8878-8885.

Pezron E, Leibler L, Ricard A, Audebert R. Reversible gel formation induced by ion complexation .2. phase-diagrams. Macromolecules. 1988; 21(4):1126-1131.

Ostergaard J, Larsen SW, Parshad H, Larsen C. Bupivacaine salts of diflunisal and other aromatic Hydroxycarboxylic acids: Aqueous solubility and release characteristics from solutions and suspensions using a rotating dialysis cell model. European Journal of Pharmaceutical Sciences. 2005; 26(3-4):280-287.

Keita G, Ricard A. Continuous swelling or collapse of chemically crosslinked gel of polyvinylalchol by borate complexation. Polymer Bulletin. 1990; 24:627-632.

Keita G, Ricard A, Audebert R, PezronE, Leibler L. The poly(vinyl alcohol)-borate system: Influence of plyelectrolyte effects on phase diagrams. Polymer. 1995; 36(1):49-54.

Higuchi T. Analysis of data on the medicament release from ointments. Journal of Pharmaceutical Sciences. 1962; 51:802-804.

Ricci EJ, Lunardi LO, Nanclares DMA, Marchetti JM. Sustained release of lidocaine from poloxamer 407 gels. International Journal of Pharmaceutics. 2005; 288(2):235-244.

Peppas NA. Analysis of fickian and non-fickian drug release from polymers. Pharmaceutica acta Helvetiae. 1985; 60(4):110-111.

Huang X, Chestang BL, Brazel CS. Minimization of initial burst in poly(vinyl alcohol) hydrogels by surface extraction and surface-preferential crosslinking. International Journal of Pharmaceutics. 2002; 248(1-2):183-192.

Conner JM, Bulgrin VC. Equilibria between borate ion and some polyols in aqueous solution. Journal of Inorganic Nuclear Chemistry. 1967; 29:1953-1961.

Roy GL, Laferriere AL, Edwards JO. A Comparative study of polyol complexes of arsenite, borate and tellurate ions. Journal of Inorganic Nuclear Chemistry. 1957; 4:106-114.

Penn SG, Hu H, Brown H, Levrilla B. Direct analysis of sugar alcohol borate complexes in plant extracts by matrix-assisted laser desorption/ionization fourier transform mass spectrometry. Analytical Chemistry. 1997; 69(1):2471-2477.

Jones DS, Woolfson AD, Djokic J. Texture profile analysis of bioadhesive polymeric semisolids: mechanical characterization and investigation of interactions between formulation components. Journal of Applied Polymer Science. 1996; 61:2229-2234.

Punnia, MA. Evaluation of pH changes in inflammation of the subcutaneous air pouch lining in the rat, induced by carrageenan, dextran and *Staphylococcus*. Journal of Oral Pathology and Medicine. 1987; 16(1):36-44.

Anderson AB, Colecchi C, Baronoski R, DeWitt TG. Local anesthesia in pediatric patients: Topical TAC versus Lidocaine. Annals of Emergency Medicine. 1990; 19(5):519-522.

Hegenbarth MA, Altieri MF, Hawk WH. Comparison of topical tetracaine, adrenaline, and cocaine anesthesia with lidocaine infiltration for repair of lacerations in children. Annals of Emergency Medicine. 1990; 19(1):63-67.

Singer AJ, Stark MJ. LET versus EMLA for pretreating lacerations: a randomized trial. Academic Emergency Medicine. 2001; 8(3):223-230.

Peppas NA, Huang Y, Torres-Lugo M, Ward JH, Zhang J. Physiochemical foundations and structural design of hydrogels in medicine and biology. Annual Review of Biomedical Engineering. 2000; 2:9-29.

* cited by examiner

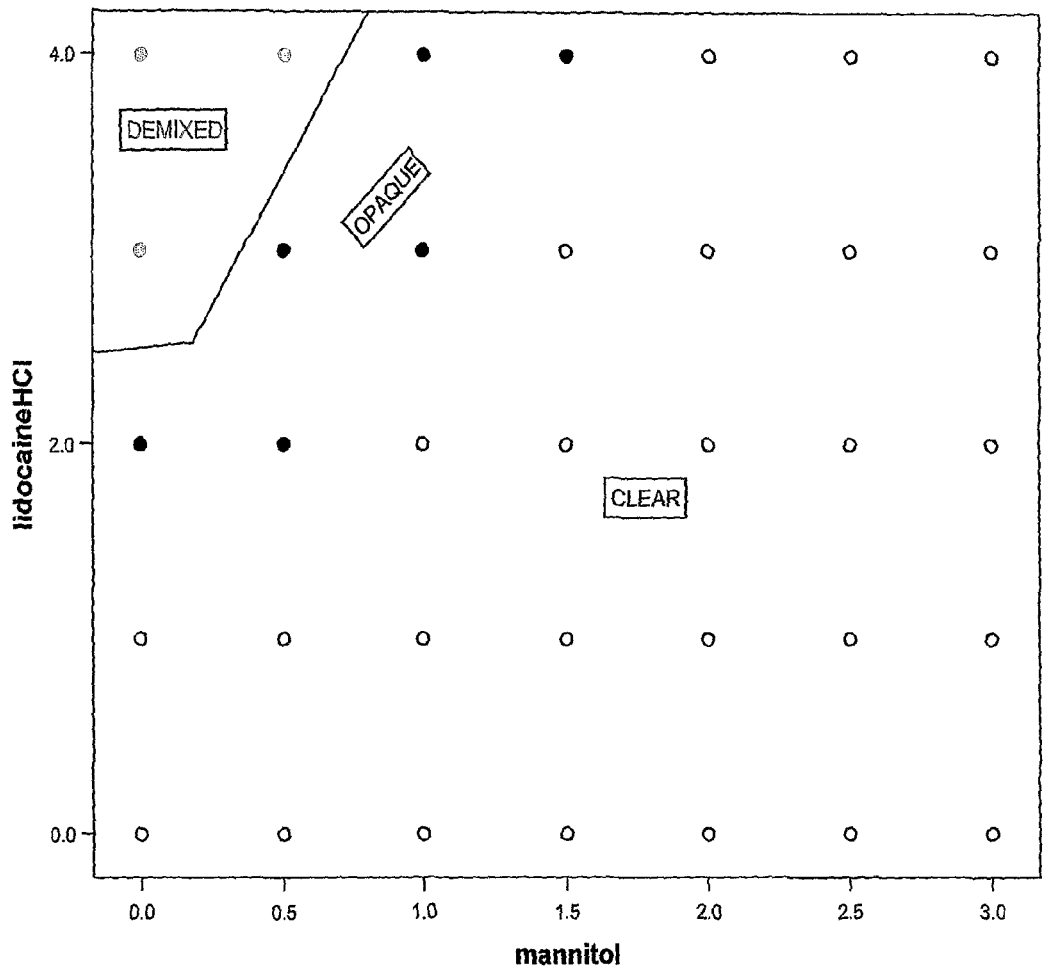
Figure3(a) – Diphase Diagram = Room temperature

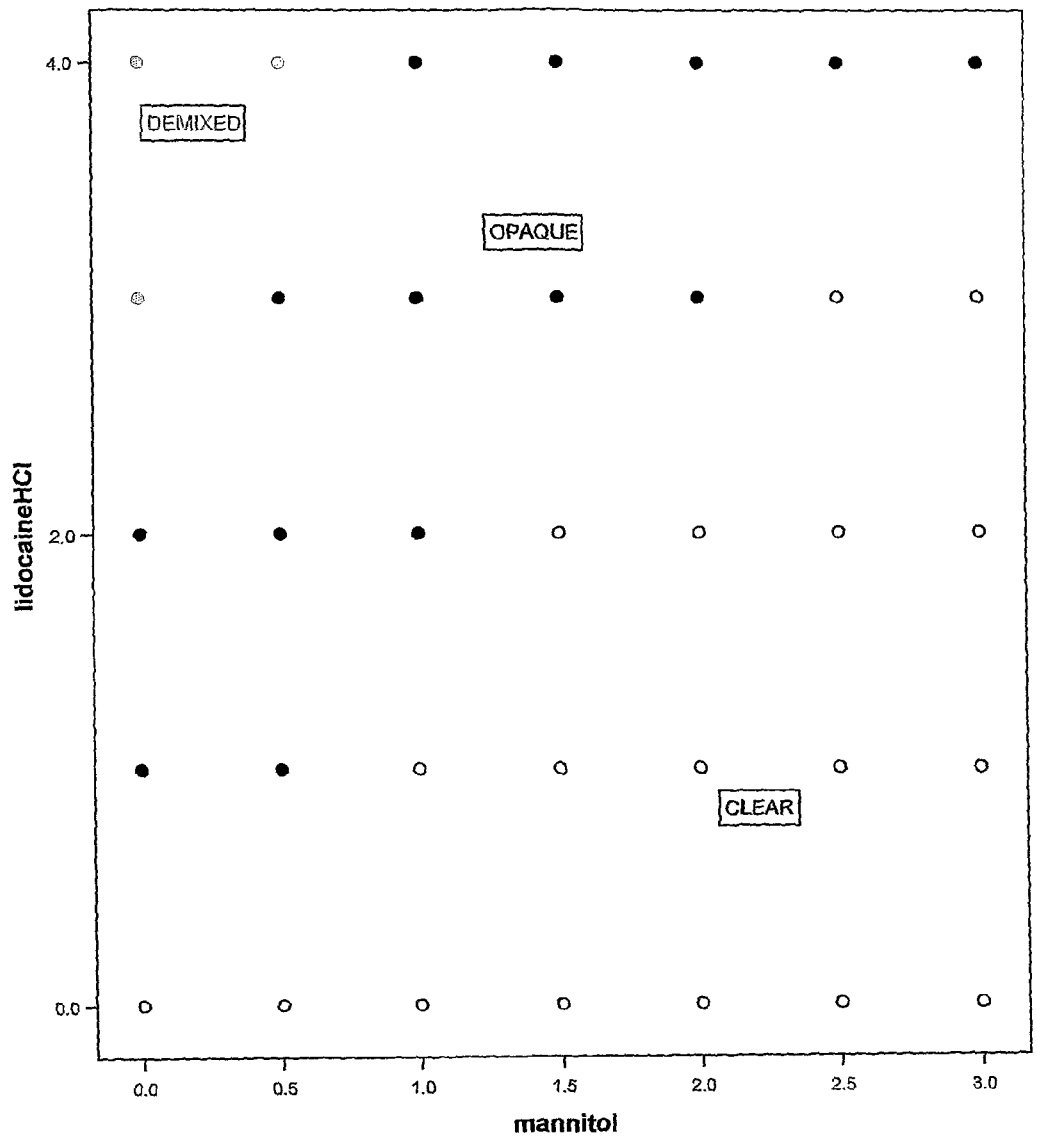
Fig (3b) – Diphase Diagram = 37°C
Graph showing the affect of D-mannitol on the solubility and appearance of 10% PVA(3)/2.5%Borax Hydrogels containing lidocaine HCL at 37°C
DEMIXED = hydrogel has separated into two phases
OPAQUE = hydrogel contains excess Lidocaine Base (above saturation)
CLEAR = Hydrogel produced is clear and homogenous

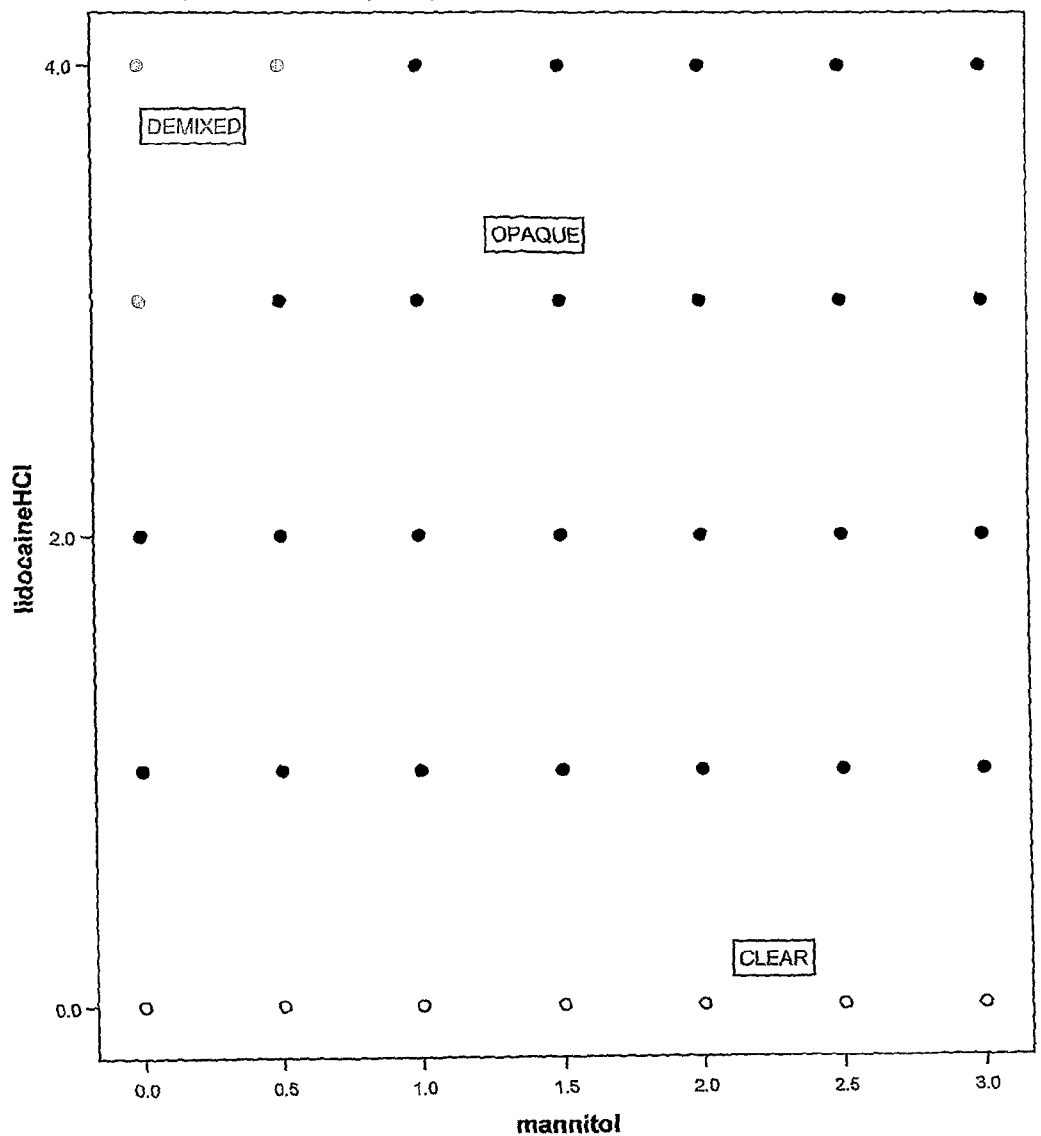

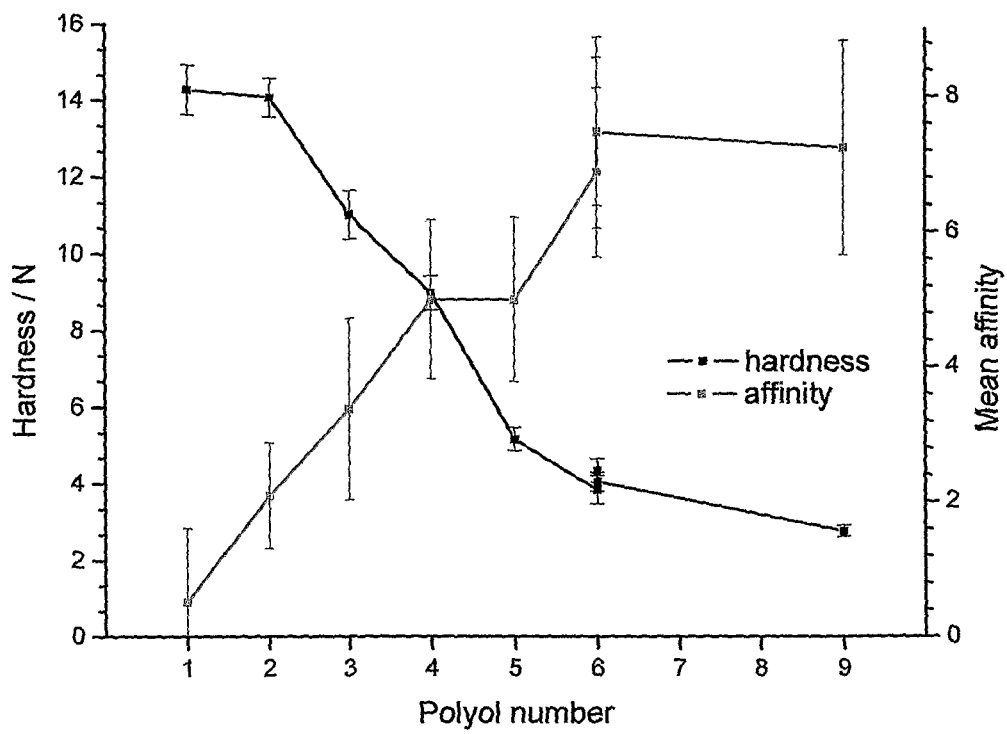
Figure 4 Relationship between polyol number (number of hydroxyl groups on modulator) and hardness of resulting gel and affinity. Affinity is defined as %[borate ions]$_f$ 0.0005 moles$^{-1}$ and is the % reduction in free borate ions for every 0.0005 moles polyol, as explained in equations (3).

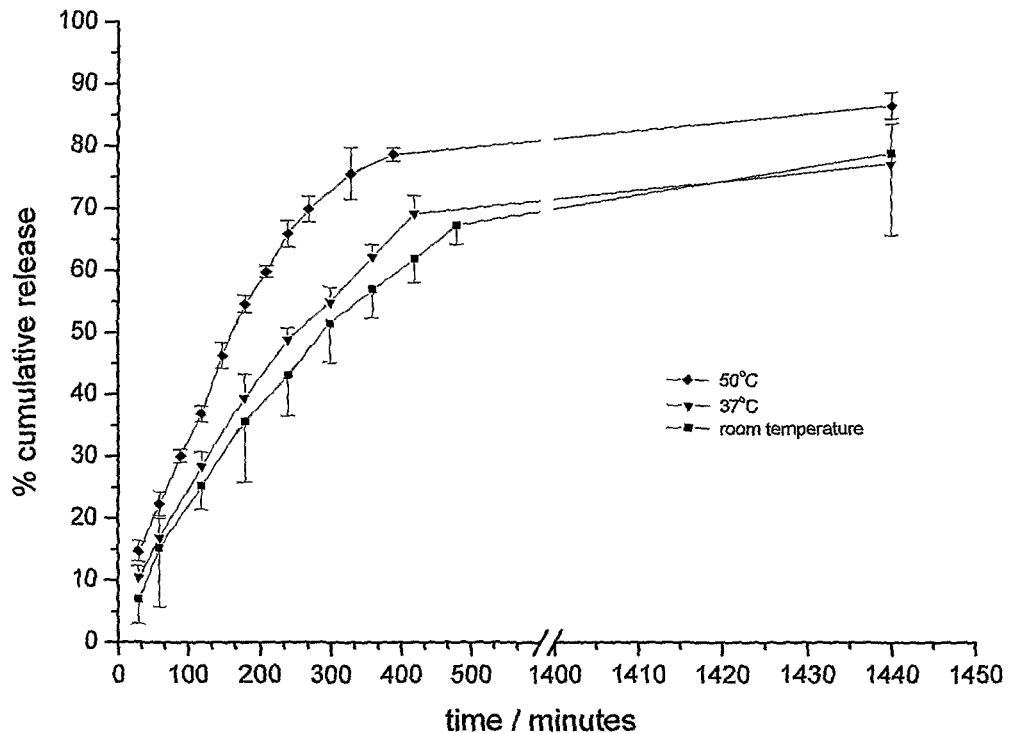
Figure 7. Cumulative release of lidocaine HCl from PVA-borate hydrogels through 8.0 μm pore cell inserts run at three temperatures, where room temperature was 26°C. Results are plotted as mean ± standard deviation (n=3; positive and negative error bars are plotted when appropriate to enhance clarity) and axis break runs from 600 to 1400 minutes.

WOUND CARE FORMULATION

The present invention relates to a gel for use in topical treatment of wounds and surface areas of the body. More specifically the invention provides a cavity filling gel formulation with low bioadhesive strength and cohesive integrity which carries at least one pharmaceutical or cosmetically active ingredient.

The invention primarily addresses the area of PVA gels subjected to reversible or partially reversible cross-linking, for use in wound care to deliver substances topically. The substances can be antibiotics or other drugs or anaesthetic or antiseptics.

Volumes of patent literature exist in this general field of gels for use in medical situations. Other attempts have been made to make a similar product unsuccessfully. For example CN1093897 relates to a surface anaesthesia film made using PVA and lidocaine in a distilled water and ethanol mix.

PVA-borate gel complexes are well known and their formation has been extensively studied in the prior art. The present invention is based upon making a gel with particular rheology and flow properties for use in wounds.

In particular there is a requirement for a gel delivery system which is semisolid, is mouldable when handled but acts like a viscous liquid when placed in a space where it has room to flow. The gel moves very slowly to fill a space that it is situated in. Also, the gel should be relatively non adhesive and can be removed intact without leaving remnants and without causing tissue trauma.

The advantages of such a delivery system for topical application of substances in a medical situation are clear and it could be assumed that if such a gel existed that it would be known in the field. No such gel based delivery systems appear to exist, with creams, ointments, powders and viscous gels presently used, being unable to fill lacerations completely without adding pressure and hurting the wound and/or requiring irrigation and some form of washing protocol during removal.

Much of the prior art in the area of polyol modulation of PVA borate gels appears to be in the area of ophthalmology rather than wound care.

The use of borate/polyol complexes to formulate ophthalmic compositions containing PVA is described in U.S. Pat. No. 5,505,953 (Chowhan). This patent teaches a method to overcome the incompatibility of PVA with borates by addition of monomeric polyols such as mannitol or sorbitol. This patent relates only to ophthalmic compositions and describes the use of PVA as a viscosity enhancer. The polyol addition stops borate and PVA coming out of solution and the complex has antimicrobial effects. The combination of ingredients described would not have the rheology and flow properties of a gel as required in the present application.

US Patent Application No. 20070059274 also relates to ophthalmic products and describes how the borate or PVA concentration may be manipulated in order to arrive at the appropriate viscosity of the composition upon gel activation (i.e., after administration to the eye). If a strongly gelling composition is desired, then the borate or polymer concentration may be increased. If a weaker gelling composition is desired, such as a partially gelling composition, then the borate or polymer concentration may be reduced. It describes that other factors may influence the gelling features of the compositions of the present invention, such as the nature and concentration of additional ingredients in the compositions, e.g., salts, preservatives, chelating agents and so on.

U.S. Pat. No. 6,444,199 entitled Solid borate-diol interaction products for use in wounds appears to be the closest single piece of prior art in the field of the invention and addresses the problem faced by the present inventors about how to fill a wound cavity effectively with a substance that can deliver an active ingredient.

This patent describes how, depending on the concentration of the polymer or polymers, the borate, and other additives, if any, the consistency of a gel can vary from somewhat viscous fluids to crisp amorphous solids. At selected concentrations of the components, the reaction products behave like self-restoring or healable solids that will flow at body temperatures. This property gives them possible value as wound-cavity fillers or wound putties. Other soluble and insoluble components can be added to impart desired properties, such as increased body-fluid absorption or fluid donation.

Although the principle use envisaged for the product of U.S. Pat. No. 6,444,199 is wound cavity-fillers, a number of other medical and non-medical markets are mentioned and these include drug delivery, prosthetics and pads (fillers or in situ-formed coatings), and the toy and possibly executive stress-reliever markets.

For use as a wound cavity-filler, U.S. Pat. No. 6,444,199 explains that the product must be firm enough to handle, yet flow at body temperature to meet wound shape in about 10 to 30 seconds. The product needs to be easy to handle and either absorb or donate moisture, or both. Materials used must be biocompatible, non-toxic, and non-cytotoxic. In this respect, samples of PVA (5% and 20%) with added borate exhibited no cytotoxicity when tested on L929 mouse fibroblasts. Importantly, this patent is not concerned with modulating the gel system to allow the inclusion of soluble active ingredients.

It is clear that there is a lot of prior art in the general field and that the problem faced by the present inventors is a known problem. However, at present a formulation having the properties of a gel as described herein for use in the wound care market including an active substance in a topical delivery product does not appear to have been disclosed or suggested before.

Wound infection may be defined as the entry, growth, metabolic activity and resulting pathophysiological effects of a microorganism upon patient tissue. Infection has been shown to impair wound healing for both acute and chronic wounds. *Staphylococcus aureus* and coagulase-negative Staphylococci are the bacteria most frequently isolated from the deep tissue of chronic wounds with *S. aureus* reported to be present in up to 43% of infected leg ulcers and in up to 88% of non infected leg ulcers.

Bacterial wound infections are treated currently using topical antibiotics, such as mupirocin, fusidic acid and neomycin or systemic antibiotics, such as the β-lactams, macrolides and metronidazole, or a combination of both. However, bacterial resistance to all of these agents has been reported widely and numerous antibiotic-resistant bacteria now exist, including meticillin-resistant *S. aureus* (MRSA) which is the primary pathogen isolated from antibiotic resistant, nosocomial wound infections. The increasing resistance of wound infections to both systemic and topical antibiotics has made effective treatment more difficult and accordingly, interest has arisen in the development of new treatment regimens.

Photodynamic antimicrobial chemotherapy (PACT) is defined as a medical treatment by which a combination of a sensitising drug and visible light causes selective destruction of microbial cells through the generation of singlet oxygen.

It is an aim of the present invention to provide a PVA-borate gel system incorporating an active ingredient such as a local anaesthetic such as lidocaine hydrochloride or antibiotics or photosensitising compounds that form part of PACT and are able to photosensitise bacterial cells or other pathogens making them amenable to the photodynamic effect.

The incorporation of active ingredients changes the suitability and rheological properties of the gel for use in a wound cavity and it is therefore a further aim of the invention to make a gel as required which has flow properties suitable for filling a wound cavity.

It is a particular aim to incorporate an active ingredient or ingredients such as lidocaine hydrochloride or the drugs used in PACT into PVA-borate hydrogels and to modulate the rheological properties that allow flow into a wound space and subsequent removal without irrigation or washing.

It is a further aim of the invention to provide PVA-borate hydrogel formulations for use in treating wounds including acute lacerations, chronic wounds and large acute wounds such as burns, wounds arising from vascular irregularities and abnormal function, wounds arising from infection by viral, fungal and bacteriological organisms, wounds where the healing is impaired by viral, fungal and bacteriological organisms, wounds on epithelised and non-epithelised tissues, wounds on mucous membranes and topical skin disorders.

According to the present invention there is provided a gel formulation suitable for topical use and in filling a wound cavity and delivering an active ingredient thereto, the gel having a pH range of 4.5 to 8.5, but preferably having a pH range of 6.5 to 7.5, having low bioadhesive strength and cohesive integrity and being formed from a polymer having extensive hydroxyl functionalities such as PVA, a cross-linker able to form associative interactions between and within said polymer, preferably but not limited to a salt form of boron that produces borate ions in aqueous solution such as borax, at least one compound which has a beneficial effect as an active ingredient in the wound and at least one modulator, the modulator being a low molecular weight species that is capable of binding borate or PVA in aqueous solution through a mono-diol or di-diol formation and can reduce the pH of PVA-borate hydrogels.

Preferably the modulator is a low molecular weight compound possessing a plurality of functional groups able to bind to borate, the functional groups being preferably hydroxyl groups and the compound being preferably a sugar alcohol and most preferably the modulator being D-mannitol.

D-mannitol belongs to a group of chemicals described a sugar alcohols. Other sugar alcohols, whilst may not being as affective as D-mannitol, can also be used to produce the same affect as D-mannitol. Additionally, other low-molecular weight molecules containing two hydroxyl groups on neighbouring carbon atoms, in the cis-position, can also be used to bind borate and reduce the pH of PVA-borate hydrogels.

Other sugar alcohols and compounds possessing the characteristics and structural features of two hydroxyl groups, in the cis-position and attached to adjacent or neighbouring carbon atoms so as to allow presentation of two or more hydroxyl functionalities in a conformation recognisable as a cis conformation, which may be used in a gel formulation of the present invention include but is not necessarily limited to malititol, dulitol, D-sorbitol, xylitol, meso-erythritol and 1,2-propandiol and glycerol.

PVA can be obtained in various grades of hydrolysis and in various molecular weights. However, the reaction with borate is no different for the PVA variants, the only thing that would change is the quantity required to produce an equivalent gel. Whilst PVA is the best candidate polymer, other polymers with extensive hydroxyl functionalities could also be used.

The PVA could have a Molecular Weight of from 1,000 to 100,000. Typically the Molecular Weight used in practice of the invention would be from 15,000 to 50,000, more preferably 20,000 to 40,000.

Typically the gel has a degree of hydrolysis of between 55 to 100%. More typically this is from 65 to 100% and more preferably from 75 to 99%.

The amount of borate used in preparing the gel depends on the type of PVA used. Typically from 0.5 to 5% borate could be used. More typically 1.5 to 4% and most preferably from 2 to 3%

The amount of modulator added in the preparation of the gel depends on the PVA and borate and the choice of modulator. Typically from 0.1 to 5% could be used. More preferably from 0.5 to 2%. For example, mannitol is a better modulator than glycerol and therefore less mannitol would be required than glycerol.

The modulator is essential to the invention as it allows the gel to maintain stability when the active ingredient is added. Without the modulator the gel viscosity collapses or the gel contracts to form hard lumps or undergoes detrimental coacervation or is seen to exhibit a separation of the polymeric and solution phases into a two-phase system by a process known as demixing. The modulator acts to re-establish the properties that allow the gel formulation to be used in cavities to administer active ingredients.

Accordingly the invention relates to the use of a modulator in a PVA-borate gel incorporating an active ingredient to maintain pH and gel structure.

The active ingredient can be any active ingredient suitable for topical administration that exhibits a degree of solubility in a PVA borate gel. A list of potential medications that could be incorporated as active ingredient is included as annex 1. The active ingredient is typically a medicament. The active ingredient can alternatively be a cosmetic or hair removal product or a therapeutic ingredient such as an essential oil or tea tree oil. The active ingredient can be a chemical compound that can be used to sensitise bacterial, fungal, viral and eukaryotic cells as part of photodynamic therapy or PACT. The active ingredient can be a bioactive peptide, an oligonucleotide, or other material used in the cosmetic regeneration of the skin surface.

The gel of the invention can be mounted on or incorporate a support such as a mesh or gauze. This may be advantageous to cover a large surface area.

In one preferred embodiment the active ingredient is a salt form of lidocaine, most preferably lidocaine hydrochloride monohydrate. Alternatively the active ingredient can be another amide local anaesthetic such as prilocalne, bupivacaine etc. or indeed any active ingredient that produces a conjugate acid and is stable in the presence of borate ions.

In an alternative embodiment the active ingredient is at least one medicament used in PACT.

The present invention also provided the use of poly-functionalised sugar alcohols to modulate the formation of a PVA-borate gel system incorporating an active ingredient wherein the gel system has flow properties that make it suitable to fill a wound cavity.

The present invention realises the combined effects of polyol sugars and lidocaine hydrochloride on the physical properties of PVA-borate hydrogels and produces an optimised formulation that would be suited to topical delivery.

The invention is illustrated with reference to the following examples and the figures and tables wherein FIG. 1 shows the affect of increasing PVA concentration on the pH of PVA-Borate hydrogels.

Figure 2:
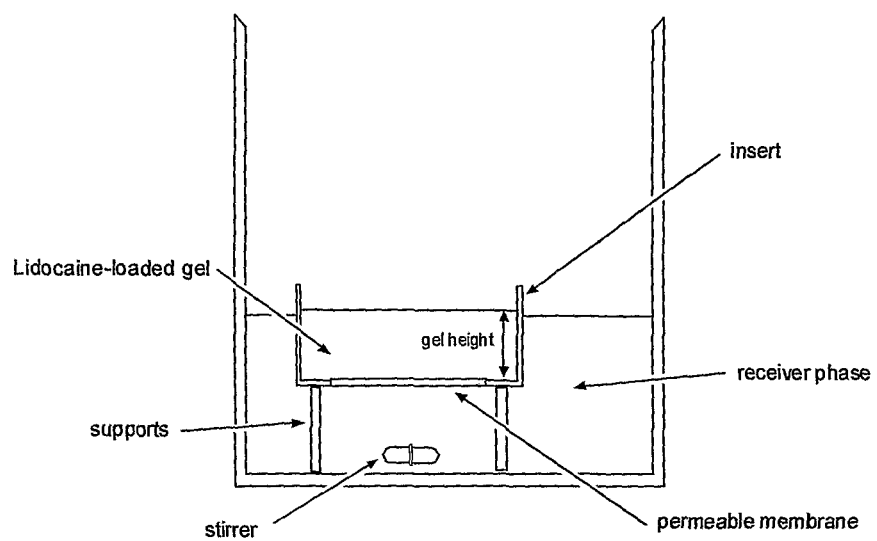

FIG. 2 shows the apparatus used to evaluate drug release.

FIGS. 3(a), 3(b) and 3(c) show the effect of D-mannitol on the physical appearance of lidocaine hydrochloride-loaded PVA-borate hydrogels.

FIG. 4 shows the effect the hydroxyl group number per polyol molecule has on hardness of the hydrogel and affinity for borate ions. The affinity is derived from measurements of pH reduction produced by defined quantities of polyol addition. Affinity reductions are an estimation of the effectiveness of the binding process between polyol and borate. The higher this measure, the stronger the association between the two and this information conveys the ability to reduce pH and viscosity of PVA-borate hydrogels. Said pH reductions permit solubilisation of intended payloads if such payloads are conjugate acid type compounds, such as lidocaine HCl monohydrate.

Figure 5A:
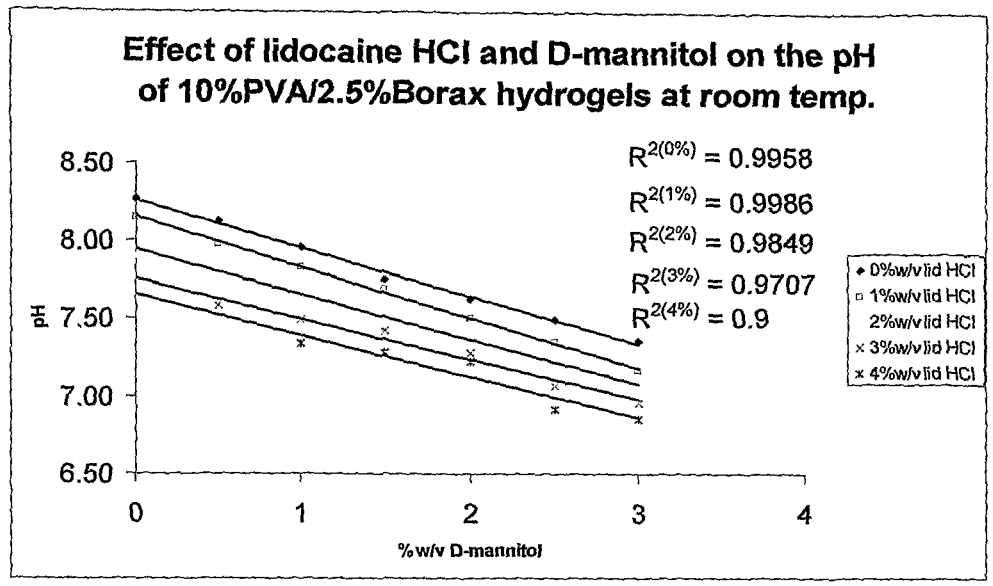

FIG. 5(a) shows the affect of D-mannitol and lidocaine HCL monohydrate on the pH of a hydrogel consisting of 10% w/w PVA and 2.5% w/w Borate. FIG. 5(b) shows the affect of D-mannitol concentration on the pH of an aqueous solution containing 5% w/v Borate).

Figure 6:
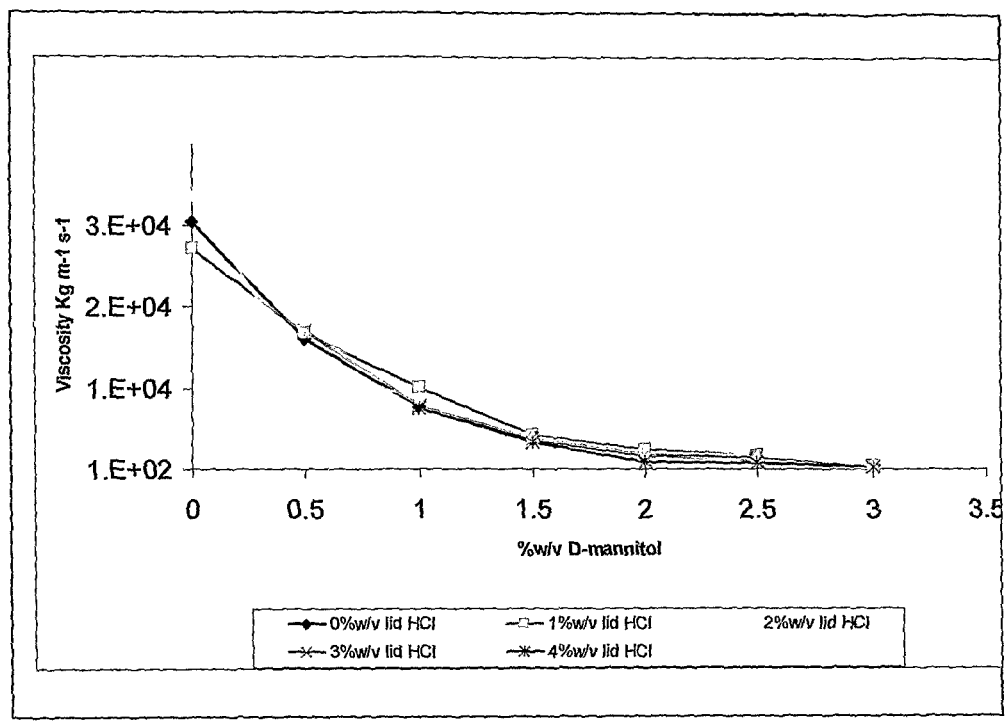
Figure 6B:
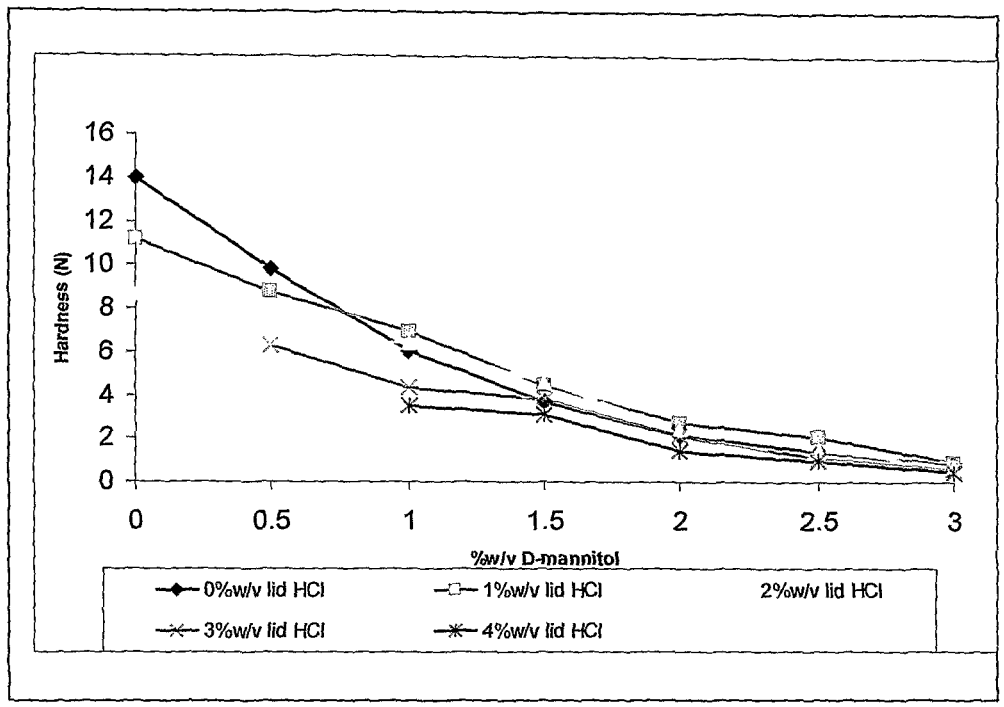
Figure 6C:
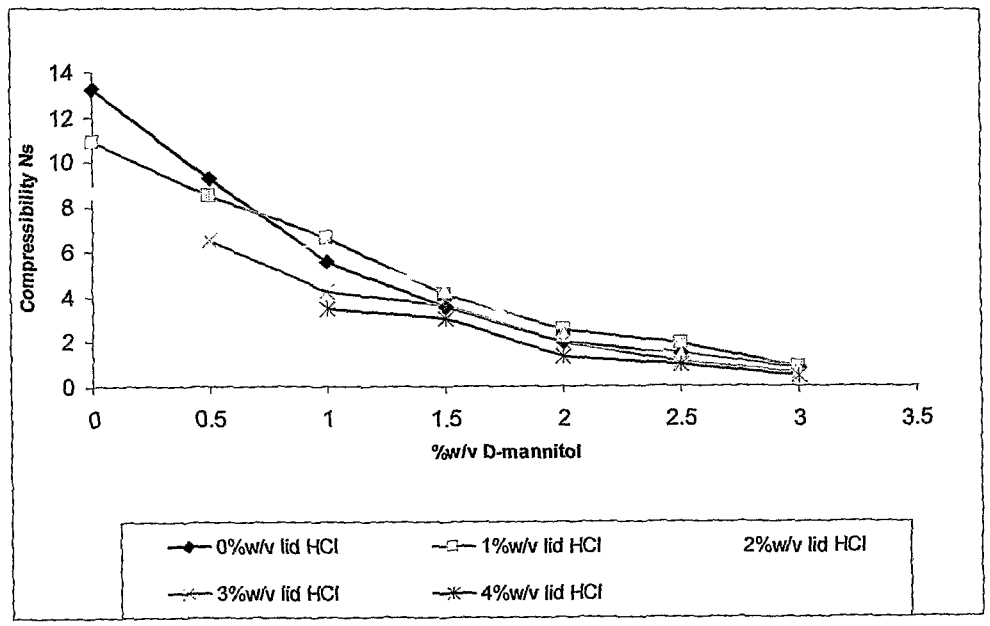

FIGS. 6(a), 6(b) and 6(c) show the effects of D-mannitol and lidocaine HCl monohydrate concentration on the viscosity, hardness and compressibility (respectively) of a hydrogel containing 10% w/w PVA and 2.5% w/w borate.

FIG. 7 shows the typical release profile of lidocaine HCl monohydrate from PVA-borate hydrogels at different temperatures resulting from evaluation of formulation six. However, other formulations produce equivalent profiles and therefore this graph can be taken as a representation of all the formulations. Cumulative release of lidocaine HCl from PVA-borate hydrogels through 8.0 μm pore cell inserts run at three temperatures, where room temperature was 26° C. Results are plotted as mean±standard deviation (n=3; positive and negative error bars are plotted when appropriate to enhance clarity) and axis break runs from 600 to 1400 minutes.

The following description outlines the properties, interactions and limitations of PVA borate hydrogels. It also gives an insight into the properties of polyols (e.g. D-mannitol) and their interaction with borax and PVA-borate hydrogels.

Derivation of six candidate formulations and their production are explained below.
Derivation of Candidate Formulations

TABLE 1

Equation (1)

$$pHp = pKa - \frac{Log10(S - So)}{So} \quad (1)$$

| Lidocaine HCl (% w/v) | pHp (aqueous soln.) | pHp (Gel) |
|---|---|---|
| 1 | ≥7.79 | ≥8.15 |
| 2 | ≥7.34 | ≥7.75 |
| 3 | ≥7.12 | ≥7.45 |
| 4 | ≥6.98 | ≥7.26 |

Equation (1) is a derivation of the Henderson-Hasselbalch equation. It is used to determine the pH (pHp) at which the free base (lidocaine) of a conjugate acid (lidocaine hydrochloride) begins to precipitate from solution. The pHp is dependent upon the solubility of the free base (So=0.015 Mol $L^{-1}$=lidocaine), the amount of conjugate acid added to solution (S=lidocaine hydrochloride) and the pKa of the conjugate acid (pKa=7.9).

Table (1) above shows examples of pHp of lidocaine hydrochloride in aqueous solution and within the environment of PVA-Borate hydrogels. The determination of the pHp in the aqueous environment is determined using the equation (1), whilst the determination of the pHp within the gel environment is derived experimentally. Whilst there are differences between the pHp determined in aqueous and gel environments (due to electrostatic interactions within the gel), it is clear that lidocaine hydrochloride has greater solubility at lower pH values e.g. 4% lidocaine hydrochloride monohydrate is insoluble at pH values >7.26 within PVA-Borate hydrogels. Therefore, as PVA-Borate hydrogels generally have pH values within the basic range (>7.5), manipulation of the hydrogels would be required in order the solubilise 4% w/w lidocaine hydrochloride and achieve a formulation suited to purpose.

FIG. 1 shows the affect of increasing PVA concentration on the pH of PVA-Borate hydrogels. It is clear, from FIG. 1, that the greater the % w/w PVA used, the lower the pH of the hydrogel. However, it is also clear that the pH produced by any of the combinations of borax or PVA are not below pH 7.26. Using the slopes of the above plots, a determination of the concentration of PVA needed to produce a hydrogel with a pH <7.26 can be made. For 0.5% and 1.0% w/w Borax, the required amount of PVA (+4% lidocaine HCL) produced a gel with undesirable flow properties (hair gel consistency). For 1.5%, 2.0% and 2.5% w/w Borax, 19%, 17% and 13.5% w/w PVA respectively, was required to theoretically solubilise 4% w/w lidocaine HCL. Whilst a gel was produced with the formulations containing 1.5%, 2.0% and 2.5% w/w Borax, they contained lidocaine precipitate and they were extremely viscous. As a result, D-mannitol was added to the formulations to reduce the viscosity and the pH (further pH reductions were required in order to fully solubilise the 4% w/w lidocaine hydrochloride).

| Formulation (1) | Formulation (2) |
|---|---|
| 19% w/w PVA | 19% w/w PVA |
| 2.5% w/w Borax | 2.5% w/w Borax |
| 4% w/w lidocaine HCl | 4% w/w lidocaine HCl |
| 0.5% w/w D-mannitol | 1.0% w/w D-mannitol |
| Up to 100 g with deionised water | Up to 100 g with deionised water |

| Formulation (3) | Formulation (4) |
|---|---|
| 17% w/w PVA | 17% w/w PVA |
| 2.0% w/w Borax | 2.0% w/w Borax |
| 4% w/w lidocaine HCl | 4% w/w lidocaine HCl |
| 0.5% w/w D-mannitol | 1.0% w/w D-mannitol |
| Up to 100 g with deionised water | Up to 100 g with deionised water |

| Formulation (5) | Formulation (6) |
|---|---|
| 13.5% w/w PVA | 10% w/w PVA |
| 1.5% w/w Borax | 2.5% w/w Borax |
| 4% w/w lidocaine HCl | 4% w/w lidocaine HCl |
| 0.5% w/w D-mannitol | 2.0% w/w D-mannitol |
| Up to 100 g with deionised water | Up to 100 g with deionised water |

Formulation (6) was produced by keeping PVA and Borax constant and increasing D-mannitol concentration until the pH was sufficiently low to solubilise 4% w/w Lidocaine HCL monohydrate.

The above formulations have varying physical and dosing properties, as shown in the table below (table (2). Whilst each constituent of the gel affects its properties, D-mannitol has the greatest influence. Therefore, as well as the six quoted formulations, other formulations can be produced by varying the concentration of D-mannitol in order to tailor the properties. For example, Formulation 2 can be produced with greater quantities of D-mannitol, which will produce a formulation with relatively greater adhesive properties and drug release kinetics, whilst having reduced hardness (less viscous) and pH.

TABLE (2)

| Formulation | pH (mean ± S.D) | Hardness (N) (mean ± S.D) | Adhesiveness (N cm$^{-2}$) (mean ± S.D) | Drug release (%) (mean ± S.D) |
|---|---|---|---|---|
| 1 | 7.18 ± 0.01 | 26.26 ± 1.91 | 0.43 ± 0.14 | 19.52 ± 0.24 |
| 2 | 7.08 ± 0.02 | 21.06 ± 1.48 | 0.71 ± 0.24 | 29.08 ± 3.51 |
| 3 | 7.08 ± 0.02 | 15.96 ± 0.93 | 0.79 ± 0.16 | 27.24 ± 1.36 |
| 4 | 7.02 ± 0.02 | 10.84 ± 1.19 | 1.51 ± 0.21 | 28.79 ± 2.01 |
| 5 | 7.03 ± 0.01 | 6.35 ± 0.01 | 1.75 ± 0.15 | 38.74 ± 7.37 |
| 6 | 7.13 ± 0.02 | 1.52 ± 0.26 | 2.21 ± 0.18 | 62.39 ± 0.77 |

Drug release describes the % lidocaine HCL released after six hours, at 37° C., from the formulation into sufficient quantity of receiver phase to achieve sink conditions. The methods of analysis are explained in more detail below.

Poly (vinyl alcohol) (PVA) is a water-soluble polymer that forms ion complexes with a range of ions and charged secondary diazo dyes, such as borate[1], vanadate[2], Congo Red[3] and cupric ions[4]. Of these ion complexes, the PVA-borate polymer-ion complex is preferred, especially in terms of biomedical compatibility, to other crosslinked networks, such as those based on vanadate, for example, that display appreciable toxicity to living tissue. The mechanism of PVA-borate complex formation has been previously elucidated through $^{13}$C and $^{11}$B nuclear magnetic resonance[5,6], with the underlying means of network formation believed to be a di-diol complexation formed between two adjacent diol groups from PVA on one hand and the borate ion on the other. The cross-link reaction is a two step procedure, whereby an initial mono-diol complexation produces a poly(electrolyte), which as a result of electrostatic repulsion, causes the expansion of individual polymer chains and produces a sterically favourable environment for the proceeding di-diol complexation reaction to occur[8].

Both inter- and intra-molecular cross-links occur as a result of the di-diol complexation reaction. Once enough inter-molecular cross-links exist, the network takes on the form of a gel system. This gelation is dependent on the number of induced temporary cross-links formed, which is dependent on the concentration of borate ions and, to a lesser extent, the concentration of PVA[9-11]. Borate ions, which form the cross-links with PVA and induce the anionic electrostatic repulsion on the chains, are produced through the aqueous dissociation of sodium tetraborate decahydrate (borax) to give equimolar portions of boric acid, tetraborate ions and sodium ions[11]. The sodium cations attenuate the overall negative charge on the poly(electrolyte) and in so doing, allow for borate-PVA cross-links to reside closer together. This effectively increases the cross-link density[21]. The overall situation, as described by Lin et al. (2005), is that the conformation of the polymer chains results from a balance between their excluded volume, electrostatic repulsion between charged complexes bound to the polymeric chains and the shielding effect of free sodium ions associated with the charged complexes[12].

PVA-borate hydrogels are of particular interest to topical drug delivery, given their unique and characteristic flow properties that have been studied extensively through dynamic viscoelastic measurements[12-16]. These properties have been attributed to the finite lifetime ($t_{life}$) of the thermo-reversible, borate mediated, cross-links. Therefore, viscoelastic properties can be explained in terms of the complex modulus (G): if the length of an observation is long (low frequency) the cross-links have sufficient time to dissociate (t>$t_{life}$); the system behaves like a viscous liquid (G">G'). In contrast, if the length of an observation is short (high frequency) the cross-links have insufficient time to dissociate (t<$t_{life}$) and the system behaves like an elastic solid (G'>G")[12, 17, 18]. Indeed, they begin to resemble the cross-links found in elastic, covalently bonded, hydrogels, such as glutaraldehyde-PVA hydrogels, which display no appreciable flow due to appreciable structural integrity maintained by cross-links with an infinite lifetime[12].

One potential use for PVA-borate hydrogels is inducing localised anaesthesia upon exposed topical surfaces, such as those uncovered during skin lacerations. At present, only unsuitable formulations such as EMLA® cream (prilocalne 2.5%: lidocaine 2.5% w/v), in-hospital prepared lidocaine-epinephrine-tetracaine gel (LET) or in-hospital prepared solution of tetracane (0.5%)-adreniline (1:20,000)-cocaine (11.8%) are used to provide local anesthesia for lacerated wounds {{93 Anderson, A. B. 1990; 92 Hegenbarth, M. A. 1990; 91 Singer, A. J. 2001;}}. Unlike PVA-borate hydrogels, these formulations offer poor residence in a wound and must be removed with a saline wash. However, as the above formulations have been shown to provide sufficient anaesthesia {{91 Singer, A. J. 2001; 93 Anderson, A. B. 1990; 92 Hegenbarth, M. A. 1990;}}, incorporation of a local anaesthetic into PVA-borate hydrogels provides a formulation that is physically suited to treatment of lacerated wounds (novel flow properties) while still having the potential to provide effective local anaesthesia.

The hydrochloride salt of lidocaine is a good choice for administration because it has a quick onset of action and a long duration of action. However, direct incorporation into PVA-borate hydrogels must take its potential effects on network stability. Addition of lidocaine HCl to PVA-borate hydrogels will effectively increase the total free ion concentration within the gel and in so doing, will potentionally have a profound effect on the internal structure of such hydrogels[21,22]. The initial poly(electrolyte) formed between borate and PVA extenuates the complexation constant between further PVA and borate interactions by way of electrostatic repulsion. However, this effect can be attenuated by the shielding effect of free ions, such as those arising from inclusion of the salt form of a drug substance[9]. Therefore, free ions reverse any reductions in the complexation constant and if the additional ionic strength is sufficient, the system cross-links prodigiously and demixes into a two phase system that is of no practical use for topical delivery.

The complexation of borate by polyols has been studied extensively[3]. Penn et al (1997) showed that D-sorbitol and D-mannitol (ligands) forms monoesters (one ligand) and diesters (two ligands) with borate ions, with the diester complex being more energetically favourable. Additionally, no ligand was seen to contain more than one borate ion, which is a consequence of electrostatic forces preventing more than one borate ion attaching to each D-mannitol/D-sorbitol molecule. Furthermore, Penn et al (1997) showed that the diol carbons involved in the monoester/diester affected the stability of the resultant complex. Through modelling studies, it was shown that the 3,4-diol carbons give rise to the most favourable complex, because on formation, the free hydroxyl groups appear orientated toward the centre and so stabilise the complex[29]. D-mannitol, for example, has a strong affinity for borate ions and if added to PVA-borate hydrogels has been shown to cause the system to fluidize[19]. This comes about as a result of D-mannitol binding up free borate ions and removing borate ions from PVA molecules. The latter process causes the network to fluidize with excess borate ions being bound by D-mannitol and borate ions bound to PVA diol functionalities being sequestered by D-mannitol. Therefore, D-mannitol will potentionally enhance the solubility of Lidocaine hydrochloride (through a reduction in pH by binding of free borate ions—Lewis base) and prevent demixing brought about by the lidocaine anions (through reduction in available borate ions).

An aspect of this invention is that D-mannitol acts as a modulator of viscosity, a modulator of pH and as a means to prevent demixing, or also recognisable as a process of syneresis, of gel and continuous phases.

Materials and Methods

Materials

Poly(vinyl alcohol) (PVA) (98-99% hydrolyzed, MW=31,000-50,000), sodium tetraborate decahydrate (Borax), lidocaine hydrochloride, xylitol, meso-erythritol, maltitol, D-mannitol, D-sorbitol, dulcitol, 1,2-propandiol, glycerol, propan-2-ol and D-mannitol were purchased from Sigma-Aldrich Company Ltd. (Gillingham, Dorset, UK). All reagents and solvents were of appropriate laboratory standard and used without further purification.

Preparation and pH Measurements of PVA-Borate Hydrogels

PVA-borate hydrogels (10% w/w PVA and 2.5% w/w borax) were prepared by combining equal volumes of separate stock solutions (20% w/w PVA and 5% w/w borax) prepared in de-ionised water. A homogenous gel was formed upon heating the mixture to 80° C. for approximately two hours, with periodic stirring. Gels were stored for 48 hours at room temperature to allow complete gelation prior to evaluation. Excipients, such as lidocaine HCL and D-mannitol, were added to the sodium tetraborate solution prior to addition to the PVA solution.

The pH of gel formulations were recorded using a Sensorex® spear-tip electrode (S175CD, Sensys Ltd, Stevenage), which is designed to penetrate and measure the pH of semi-solid systems. Measurements of pH in borax solutions (5% w/v), following successive additions of D-mannitol ($5.0 \times 10^{-3}$ mole), were recorded using the same electrode apparatus.

Texture Analysis

Evaluation of the mechanical properties of PVA-borate hydrogels was performed using a TA-XT2 Texture Analyzer (Stable Micro Systems, Haslmere, UK) in texture profile analysis (TPA) mode. Formulations were placed in poly(propylene) containers (44 mm diameter×55 mm depth) (Sarstedt©, Wexford, Republic of Ireland) with any air bubbles in the gels removed upon standing at ambient temperature (>6.0 h) prior to investigation. The tubular probe (10.0 mm in diameter and 150.0 mm in length) was compressed twice into each sample to a depth of 15.0 mm at a rate of 10.0 mm s$^{-1}$, with a 15.0 s delay between compressions. Four replicate measurements were made in each case at ambient temperature.

Hardness and compressibility, which have previously been used to define the mechanical properties of hydrogels were derived from the force-time plots produced by the TPA analysis[30]. Those skilled in the art of TPA, will be familiar with production of said force-time plots and derivation of hardness and compressibility data from aforementioned data. Hardness, the force required to achieve a given deformation, was determined by the force maximum of the first positive curve of the force-time plot[30]. Compressibility, the work required to deform the product during the first compression of the probe was determined by the area under the first positive curve of the force-time plot[30].

Viscosity Analysis

The viscosity of PVA-borate hydrogels was determined at a constant shear force using the falling sphere technique and applying the Stoke's equation, as shown in Equation 2;

$$\eta = \frac{2(\Delta P) g a^2}{9v} \quad (2)$$

where η is the viscosity at constant shear force, ΔP is the difference in density between the sphere and the gel, g is the acceleration due to gravity (9.807 m s$^{-1}$), a is the radius of the sphere and v is the experimentally derived velocity of the sphere through the test gel. Constant velocity was derived from the time required for the metallic sphere to travel a defined distance into the gel. To ensure measurements were taken upon attaining terminal velocity, the defined distance was measured from a point when the sphere has depressed 2.0 cm into the gel and was stopped 5.0 cm before the sphere has reached the bottom of the container. The viscosity was determined for each hydrogel and subsequently repeated for replicate samples (n=4).

Comparison of Polyol Affinity for Borate Ions

The following polyols were used in this investigation; maltitol, dulcitol, D-mannitol, D-sorbitol, xylitol, meso-erythritol, 1,2-propanediol, glycerol. Additionally, the affect of propan-2-ol was also investigated. The affinity of each polyol for borate was estimated using direct titrimetry and by analysis of gel characteristics. In the former method, incremental additions (1.0 ml) of a 0.5 M solution of polyol was added to 100.0 ml of 5% w/v Borax solution and the pH recorded. The reduction in free borate and subsequent percentage reduction per $5.0 \times 10^{-3}$ moles of polyol were calculated using Equation 3;

$$10^{(pH-pKa)}[H_3BO_3]_0 = [B(OH)_4^-]_f \quad (3)$$

where, $[H_3BO_3]_0$ is the concentration of boric acid, $[B(OH)_4^-]_f$ is the concentration of free borate ions and $pK_a$ is the $pK_a$ of boric acid (derived from the initial pH of the 5% w/v borax solution). The equation assumes that boric acid concentration does not change with addition of the polyol, and that only monoborate ions occur at the concentration of borax used in the analysis (i.e. no borate aggregates exist). These assumptions are consistent with work of other researchers[27,28].

Additionally, the effect of the polyols on the concentration of free borate ions within the hydrogel was estimated using changes in the pH of the gel after addition of a defined polyol. Standard hydrogels of 10% w/w PVA and 2.5% borax were produced containing each polyol at a concentration of 0.1 Molar. The pH of each gel was measured upon equilibration, with each measurement performed for four samples (n=4). Similarly, the changes in gel hardness arising from variations in free borate induced by polyol addition were determined using texture profile analysis, as described above. As before, four replicate measurements were made in each case at ambient temperature (n=4).

In Vitro Release Studies

One dimensional drug release was evaluated using cell culture inserts (Nunc®, No. 137508, Rochester, USA) constructed with an integral poly(carbonate) membrane of 8 μm pore size, as shown in FIG. 2. Inserts were used as the gel-loaded donor phase suspended in an aqueous receiver phase. Cell inserts were modified to become free standing by raising the standard base by 1.0 cm in height, which also ensured effective stirring under the receiver side of the permeable membrane. The hydrogel (4.00 g) was added to the inserts and its height and weight within the insert recorded prior to, and after, in vitro release investigations.

Release experiments commenced once gel-loaded inserts were placed in 100 ml of receiver phase, which was stirred at 250 rpm. A phosphate buffer (BP 1999, pH=6.8) was used as the receiver phase to mimic the slightly acidic environment of an infected/inflamed wound[31]. Sink conditions were maintained throughout the release experiment by ensuring that the total drug possible in the receiver phase never exceeded 10% of its solubility in this compartment. At defined time intervals, 5.0 ml of receiver phase was removed, replaced by fresh buffer and lidocaine concentration determined spectrophotometrically at 265 nm (Carey® 50 scan UV-Visible spectrophotometer). In vitro release studies were carried out at ambient temperature, 37° C. and 50° C. Once complete, the gel height and weight were measured again. Each release experiment was performed three times (n=3).

Data Treatment and Statistical Analysis

To elucidate the drug release mechanism as a function of temperature, the drug release data was fitted to the exponential equation described by Peppas and shown in Equation 4[25];

$$\frac{M_t}{M_\infty} = kt^n \quad (4)$$

where $M_t$ is the amount of drug released at time t, $M_\infty$ is total amount of drug in the system, $M_t/M_\infty$ is the fraction of dug released at time t, k is the kinetic constant that incorporates the properties of the polymeric system and the drug and n is the diffusional exponent of the drug release, used to characterise the drug transport mechanism. Therefore, calculation of the release exponent n allows for the determination of the mechanism of diffusion in the polymeric systems. Only the region of the first 60% of drug release with a stable release profile was used to determine n i.e. initial region of high flux was excluded from the determination of n.

The effects of D-mannitol and lidocaine hydrochloride on the hardness, compressibility and viscosity of PVA-borate hydrogels were evaluated using a two-way analysis of variance (ANOVA) with a 5×7 factorial design. Post-hoc analysis, namely Tukey's test, was employed for comparison of the means of the individual groups. Additionally, the effect of each polyol on hardness of standard hydrogels was evaluated using ANOVA with a 1×7 factorial design. With Tukey's test again being employed for post-hoc analysis. P<0.05 denoted significance for all statistical comparisons.

Results

The effect of D-mannitol on the physical appearance of lidocaine hydrochloride-loaded PVA-borate hydrogels is shown in FIGS. 3 (a), 3(b) and 3(c). A formulation containing 10% w/w PVA and 2.5% w/w sodium tetraborate was chosen for this investigation. This formulation was chosen because it possessed high degrees of hardness, compressibility and viscosity and thus could accommodate any reductions in the physical properties brought about by D-mannitol or lidocaine hydrochloride. From examination of the results it is clear that D-mannitol increases the solubility of lidocaine hydrochloride, as shown by the clear gel region seen in the upper right-hand corner of the phase diagram (FIG. 3(a)). Additionally, D-mannitol prevents the demixing effect seen in PVA-borate hydrogels brought about by lidocaine hydrochloride concentrations that exceed 3.0% w/v. Furthermore, it is an important finding that as temperature is increased from ambient temperature through 37° C. to 50° C., the solubility of lidocaine hydrochloride is reduced progressively. This is evident in the progressive movement of the opaque-clear interface region that eventually encompasses all lidocaine HCl concentrations (FIG. 3(c)).

Table 3 shows the effect of each polyol on free borate concentration, pH and hardness of the test hydrogel (10% w/w PVA and 2.5% w/w borax).

TABLE 3

| polyol | % reduction in free borate/0.0005 moles | pH of hydrogel with 0.1 M polyol | Hardness (N) |
|---|---|---|---|
| Malititol, $C_{12}H_{24}O_{11}$ 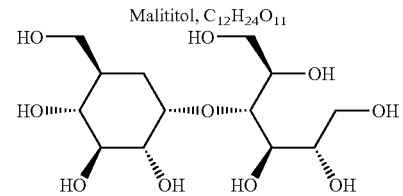 | 7.25 ± 1.59 | 7.63 ± 0.019 | 2.79 ± 0.14 |
| Dulitol, $C_6H_{14}O_6$ 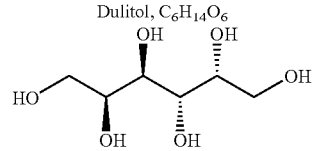 | 7.46 ± 1.41 | 7.67 ± 0.015 | 3.87 ± 0.38 |
| D-mannitol, $C_6H_{14}O_6$ 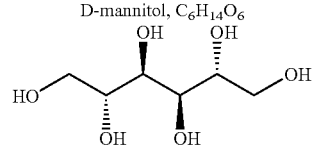 | 7.47 ± 1.10 | 7.74 ± 0.023 | 4.07 ± 0.25 |

TABLE 3-continued

| polyol | % reduction in free borate/0.0005 moles | pH of hydrogel with 0.1 M polyol | Hardness (N) |
|---|---|---|---|
| D-sorbitol, $C_6H_{14}O_6$ | 6.87 ± 1.25 | 7.79 ± 0.02 | 4.37 ± 0.31 |
| Xylitol, $C_5H_{12}O_5$ | 4.97 ± 1.21 | 7.95 ± 0.038 | 5.18 ± 0.31 |
| Meso-erythritol, $C_4H_{10}O_4$ | 4.97 ± 1.17 | 8.10 ± 0.01 | 9.01 ± 0.45 |
| 1,2-propandiol, $C_3H_8O_2$ | 2.08 ± 0.78 | 8.39 ± 0.02 | 14.10 ± 0.5 |
| Propan-2-ol, $C_3H_8O_1$ | 0.51 ± 1.09 | 8.393 +/− 0.012 | 14.30 +/− 0.65 |
| Glycerol, $C_3H_8O_3$ | 3.36 ± 1.34 | 8.17 +/− 0.022 | 11.06 +/− 0.62 |
| No polyol | — | 8.41 +/− 0.51 | 14.58 +/− 0.89 |

The overwhelming trend is that affinity for borate is increased as the number of hydroxyl groups per molecule is increased. There is a clear increase in the reduction in free borate (as seen by the reduction in pH) and hardness as this structural feature is incremented. In fact, each sequential reduction in hydroxyl group number per molecule, that is, going from 6 to 5 to 4 and so on, resulted in significant increases in hardness of the hydrogel, as shown in FIG. 4. For example, the hydrogel containing 0.1 Molar erythritol (four hydroxyl groups per molecule) was shown to have significantly greater hardness (p<0.001) and compressibility (p<0.001) than the hydrogel loaded with 0.1 Molar xylitol (five hydroxyl groups per molecule). If the number of hydroxyl groups per molecule was kept constant, as in dulcitol, D-mannitol and D-sorbitol, no significant difference in hardness was observed. Furthermore, the affect of hydroxyl groups per molecule on hardness was shown to be inversely related to affinity of the polyol for borate ions. This is illustrated by the decreasing trend in borate affinity as the number of hydroxyl groups per molecule is decreased.

Additionally, hydrogels loaded with 0.1 Molar propan-2-ol and 1,2-propandiol, with one and two hydroxyl groups per molecule respectively, was shown to have no affect on the hardness of the hydrogel when compared to the hydrogel containing no polyol.

The effect of D-mannitol and lidocaine HCl incorporation on the pH of PVA-borate hydrogels is shown in FIG. 5(a). It is clear that both D-mannitol and, to a lesser extent, lidocaine hydrochloride reduce the pH of the tested hydrogel (10% w/w PVA and 2.5% w/w borax). Importantly, increasing D-mannitol causes a linear reduction in pH. This can be compared to the affect of D-mannitol on the pH a 5% w/v borax solution, as shown in FIG. 5(b), which again displays inverse proportionality between pH and D-mannitol concentration.

The effects of D-mannitol and lidocaine HCl incorporation on hardness, compressibility and viscosity are shown in FIGS. 6(a), 6(b) and 6(c), respectively. Again, the concentration of PVA and Borax was kept constant (10% w/w PVA and 2.5% w/w borax). In the absence of lidocaine HCl, increasing D-mannitol by 0.5% w/v increments caused a significant reduction between steps in the hardness and compressibility of PVA-tetraborate hydrogels up to a total concentration of 2.5% w/v D-mannitol. For example, the hydrogel containing 0.0% w/w lidocaine hydrochloride and 1.5% w/w D-mannitol was shown to possess significantly greater hardness (p<0.001) and compressibility (p<0.001) than the hydrogel containing 0.0% w/w lidocaine hydrochloride and 2.0% w/w D-mannitol. However, increasing D-mannitol by 0.5% w/w between 2.5% w/v and 3.0% w/v did not produce a significant effect on hardness and compressibility. The trend seen in hardness and compressibility is also evident for viscosity; except that once D-mannitol exceeds 2.0% w/v no further significant reduction is seen. Furthermore, from the statistical analysis, it was clear there existed an interaction between lidocaine and D-mannitol in that the effect of adding both into the same gel is not simply an additive reduction in the physical properties i.e. a saturation point was evident, where, at certain concentrations of D-mannitol, adding lidocaine hydrochloride had no effect on the physical properties of the hydrogel. (two-way analysis of variance can identify if a variable has a significant effect and if two variables are interacting with each other—once an interaction is found you must treat every group separate to elucidate the nature of the interaction—very time consuming for a factorial design of 5×7=35 individual groups). With respect to hardness and compressibility, increasing lidocaine hydrochloride by 2% w/w (up to 4%) causes a significant reduction in the hardness and compressibility of the hydrogels when the concentration of D-mannitol is ≤1.5% w/v. For example, the hydrogel containing 1.0% w/w lidocaine hydrochloride and 1.0% w/w D-mannitol was shown to posses significantly greater hardness ($p<0.001$) and compressibility ($p<0.001$) than the hydrogel containing 3.0% w/w lidocaine hydrochloride and 1.0% w/w D-mannitol. However, when the concentration of D-mannitol is greater than 1.5% w/w (saturation point) varying lidocaine hydrochloride concentration from 0-4% w/w does not have a significant affect on the hardness and compressibility of the hydrogel. This trend is also apparent with respect to viscosity except that the apparent saturation concentration of D-mannitol for lidocaine hydrochloride is 0.5% w/w.

The in vitro release profiles are shown in FIG. 7. In this part of the study, the loadings of lidocaine HCl (4.0% w/w), D-mannitol (2.0% w/v), sodium tetraborate (2.5% w/v) and PVA (10.0% w/v) were kept constant, with temperature being the only changing variable. It is evident that increasing temperature causes not only an increase in the release rate of lidocaine hydrochloride, but also alters the mechanism by which the drug vacates the system. As can be seen in Table 4, the mean time taken for 60% of drug to be released ($t_{60\%}$) decreases to 210 minutes for release at 50° C. Interestingly, the release exponent, as calculated using the natural log plots of the drug release studies and applying equation 4, also increased as temperature was increased.

TABLE 4

Time to achieve 60% release ($t_{60\%}$) and corresponding release exponent as calculated using Equation 4

| Temperature/° C. | $t_{60\%}$/minutes | release exponent |
|---|---|---|
| ambient | 390.48 ± 14.79 | 0.668 ± 0.095 |
| 37 | 336.59 ± 4.30 | 0.711 ± 0.025 |
| 50 | 238.42 ± 2.06 | 0.825 ± 0.012 |

These results indicate a change in drug release mechanism where diffusion is the predominant mechanism when the temperature is low, changing steadily to one approaching zero-order kinetics as the temperature rises. Indeed, the profile at 50° C. shows evidence of the lidocaine release approaching linearity for the first 60% of the drug's release Vs time.

Discussion

PVA-borate polymeric matrices are of novel interest because they offer a unique set of characteristic flow properties that make them an effective delivery vehicle of local anaesthetics into cavernous wounds. Their low bioadhesive strength and cohesive integrity ensure that the system can be removed as an intact piece and without inflicting further trauma. The formulation and drug release of lidocaine HCl from polymeric matrixes has been studied extensively[20,24]. It has been shown by this work that without the incorporation of D-mannitol into the analyzed PVA-borate polymeric hydrogel, lidocaine hydrochloride compatibility would be poor i.e. either a precipitate is formed or the hydrogel demixes. An important finding of this work has been to show that D-mannitol is able to modify the cross-linking dynamics of these hydrogels and therefore alleviate ionic-induced network collapse or prevent precipitate formation induced by lidocaine HCL. Indeed, it was shown that an incorporation of up to and exceeding 4.0% w/v lidocaine HCl in a homogenous gel was possible. It should be remembered that lidocaine HCl dissolves in water to form an acidic solution, as shown below.

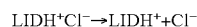

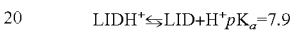

The conjugate acid LIDH$^+$ will dissociate slightly to form the relatively insoluble lidocaine base LID (solubility=0.015 mol L$^{-1}$). The formation of the lidocaine base and any subsequent precipitation can be related to initial lidocaine HCl concentration and pK$_a$ by Equation 1[20];

$$pH_p = pK_a - \text{Log}_{10}\left(\frac{S - S_0}{S_0}\right) \quad (1)$$

where pH$_p$ is the pH above which the drug begins to precipitate from solution as the free base, pK$_a$ is the pK$_a$ of lidocaine hydrochloride (=7.9), S$_0$ is the solubility of lidocaine base (0.015 mol L$^{-1}$) and S is the concentration of lidocaine hydrochloride dissolved in solution. According to equation (1), homogenous solutions are favoured at low pH and dissolved drug is only found as the free base above pH 7.9. Therefore, given the inherent alkalinity of PVA-borate hydrogels (5% w/v Borax solution is a buffer at pH 9.3 at 20'C), producing a solution of lidocaine HCl at therapeutic concentrations in such gels is potentially unattainable.

The increased solubility of lidocaine hydrochloride in PVA-borate hydrogels, brought about by D-mannitol, as shown in FIG. 3, as a result of D-mannitol binding up free borate ions in the aqueous environment of the gel[19]. By binding up borate ions, d-mannitol decreases the pH of the hydrogel and subsequently enhances the solubility of lidocaine HCL. It can be seen from Table 1 that the determining factor of borate affinity among the polyols, is the number of hydroxyl groups per molecule. The more available hydroxyl groups, the greater the possible association and formation of a monoester and the more likely there will be the formation of energetically favourable complex, as seen with borate and diol carbons 3 and 4 of D-mannitol. Additionally, isomers such as Dulcitol, D-sorbitol and D-mannitol have similar affinities for borate because they have an equivalent density of hydroxyl groups on an open chain structure. This is confirmed by the affect of 0.1 Molar Dulcitol, D-mannitol or D-sorbitol on the hardness of the hydrogels, where no significant difference was shown (FIG. 3). Malititol, with the largest hydroxyl density per molecule, has been shown to have the greatest affinity for borate ions. It should be borne in mind, however, that malititol is a disaccharide and it is conceivable that two borate ions could bind to each ligand. Although malititol has a greater affinity for borate ions overall, there is no advantage to using it as its larger molecular mass, necessitates a greater mass to be included in the formulation in order to achieve the same binding as an equivalent amount of D-mannitol. Following on from this, D-mannitol was chosen as the polyol of choice, because of its affinity, ready availability and regulated pharmaceutical status (mannitol BP).

Figure 5:
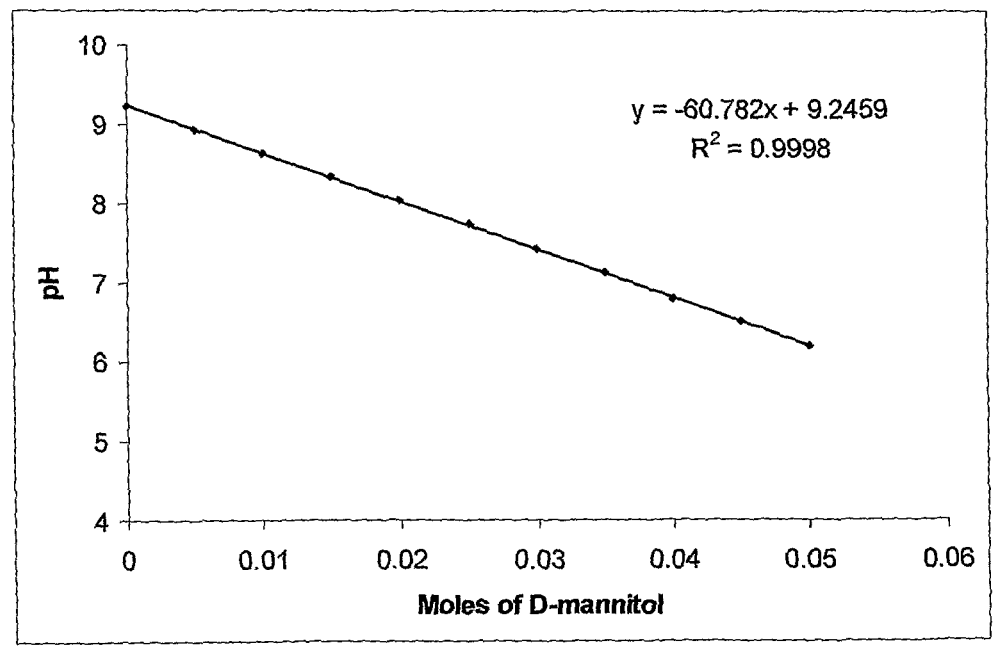

By binding up free borate ions, D-mannitol effectively drives the pH of the aqueous environment down, as confirmed in FIG. 5, which results in the increased solubility of lidocaine HCl. Furthermore, demixing, as brought about by high lidocaine HCl concentrations (≥3.0% w/w) is actively inhibited by D-mannitol, an effect that can be explained in terms of the complexation constant between PVA and borate ions. It should be remembered that demixing is brought about by an increase in the complexation constant with PVA due to an increase in ionic strength. The increase in ionic strength, as a result of added lidocaine HCl, lessens the repulsive effect of the poly(electrolyte) network, which in turn causes an increase in complexation constant and a resultant increase in the borate PVA cross-linking. This increase in cross-link density results in phase separation and demixing[9,19]. It follows, therefore, that if D-mannitol can mop up free borate, the latter are not available for binding and constriction of the network is avoided. It is important to note that, in absence of D-mannitol, only lidocaine HCL concentrations ≥3.0% w/w cause demixing because lower concentrations do not produce lidocaine-H+ cations (conjugate acid) because the environmental pH of the hydrogels are greater than 7.9.

This study has shown that the solubility of lidocaine HCl in PVA-borate systems decreased as the temperature was increased, as shown in FIG. 3. This is an important finding and can be attributed to the breakdown of the internal structure of PVA-borate hydrogels upon heating, whereupon the density of di-diol cross-links reduce and the available free borate ions increase. This increase in free borate ions elevates pH, causing a reduction in the solubility of lidocaine HCl. The end result is a precipitate formed once the saturation solubility of the lidocaine base is exceeded (0.015 mol $L^{-1}$).

It is well described in the literature that D-mannitol has a greater affinity for borate ions relative to PVA, which means that D-mannitol will progressively compete and remove borate ions from PVA/borate hydrogels causing the system to fluidize[19]. The progressive reduction in the cross-link density of PVA-borate hydrogels by increasing D-mannitol concentration is evident from the texture and viscosity analysis. Physical characterisation showed that increasing D-mannitol in 0.5% increments up to a final concentration of 2.5% w/w for texture analysis and up to 2% w/w for viscosity determination produced significant reductions in both (FIG. 6). This reduction in the physical properties of the hydrogel can be attributed to the successive sequestering of both free borate and borate bond to PVA molecules by D-mannitol. This binding of borate ions to D-mannitol appears to reach a saturation point at high concentrations of D-mannitol; e.g. there is no significant reduction in viscosity through increasing D-mannitol from 2-3% w/w. This saturation affect is explained in terms of the logarithmic reduction in borate ions as D-mannitol is increased. Effectively, at high concentrations of D-mannitol (>2.0% w/w), further increases cause a small change in the percentage of bound borate ions. D-mannitol causes a linear reduction in pH, which, according to the Henderson-Hasselbalch equation, causes a log reduction in free borate ions. Therefore, at high D-mannitol concentration (>2% w/w), there is only a small amount of free borate ions and adding additional D-mannitol will have a minimal effect on the integrity of the gel. However, although it is clear from the physical analysis that increasing D-mannitol progressively reduces borate ions bound to PVA, it is not clear what percentage of borate ions is bound to PVA or D-mannitol. In order to elucidate the relative binding proportions, more sophisticated analysis, such as $^{11}B$ NMR would be required. Furthermore, at low levels of D-mannitol, increasing lidocaine hydrochloride by 2% w/w increments significantly reduces the physical properties of PVA-borate hydrogels. This can be attributed to the production of $H_3O^+$ ions by the conjugate acid lid-$H^+$. The $H_3O^+$ ions react with the borate ions (Lewis base) to produce boric acid which results in a net reduction in the free borate ions. The reduction in free borate ions produces a reduction in the bound borate ions which in turn causes a reduction in the physical properties of the system. This affect is limited by high levels of D-mannitol, because at such conditions free borate ions are at a very low concentration.

The investigation of drug release was carried out on a formulation judged to possess favourable flow characteristics for topical drug delivery. Over the three temperatures tested, similar patterns were observed, namely an initial region of high flux followed by a stable phase of release. The initial high flux can be attributed to an initial burst effect, known to occur over a short period of time, being unpredictable and often occurring in hydrogels as a result of higher surface concentrations brought about by migration of the drug to the surface[26]. Ongoing flux took about 60 minutes to reach a more stable profile. It was interesting to note that the duration of initial anomalous flux was temperature dependent, with higher temperatures producing a more stable profile after a shorter duration, indicating that this initial phase can not simply be explained in terms of a burst effect. Effects arising from system swelling and forming an equilibrium with the surrounding environment may be attributive. In any event, the large release of lidocaine at the beginning of the release profile could be construed as beneficial, because the initial high levels will offer a quick and effective local aesthetic effect to a target wound site.

The region of stable flux (up to a maximum of 60% of drug released) was used to determine the mechanism of diffusion through by calculation of the release exponent, which were seen to approach 1.0 as the environmental temperature was increased. This temperature-induced alteration in the release mechanism can be explained on the basis of the concentration of free borate ions, which increase as the temperature is increased. The ensuing elevation in pH forces lidocaine base to form a precipitate once saturation is reached. This nascent precipitate acts as a drug reservoir that constantly replaces the soluble lidocaine that diffuses out of the system. Indeed, the hydrogel can be observed to turn opalescent in appearance when warmed. As a result of the reservoir effect, a constant diffusion gradient can be maintained effectively whilst the precipitate is present. This effect was most evident for the release at 50° C. (n=0.83), where the precipitate was still observed throughout the hydrogel even after 60% of the drug had been released. In contrast, cooler temperatures resulted in both diminutions in precipitate and the release exponent until, at ambient temperature (n=0.66), no precipitate was evident. As a consequence, the hydrogel at ambient temperature contains drug completely dissolved in a hydrophilic matrix. Therefore, it is not surprising that diffusion through this system approaches a square root of time relationship (n=0.5), as this relationship is often seen in polymer matrixes where the drug is completely dissolved in the system.

In conclusion, D-mannitol was shown to be an effective and requisite excipient for formulating lidocaine HCL into PVA-borate hydrogels. D-mannitol was shown to circumvent network constriction induced by ionic effects upon adding a hydrochloride salt of a drug substance. Formulation 6 (4% lidocaine, 2% D-mannitol, 10% PVA and 2.5% borax) was shown to offer an effective delivery system, which was characterised by an initial burst release and a drug release mechanism dependent on temperature, changing from a diffusion-controlled system to one with the properties of a reservoir system. The novel flow properties and innocuous adhesion of PVA-borate hydrogels mean they are suited for the drug delivery to exposed epithelial surfaces, such as lacerated wounds.

EXAMPLE 2

Gel Formulation including drugs for Photodynamic antimicrobial chemotherapy (PACT) which is defined as a medical treatment by which a combination of a sensitising drug and visible light causes selective destruction of microbial cells through the generation of singlet oxygen. Such a gel can be added to wounds to prevent and treat infection and infestation such as that caused by MRSA.

A typical formulation would be prepared as for lidocaine and include medicaments such as haematoporphyrin derivative, chlorins and bacteriochlorins, phthalocyanines and derivatives there off, benzoporphyrin derivatives, derivatives of 5-aminolaevulinic acid (ALA), purpurins, porphycenes, pheophorbides and verdins, psoralens and their derivatives, anthracycline compounds and their derivatives, phenothiazinium compounds such as methylene blue and toluidine blue, cyanines such as merocyanine 540, acridine dyes, derivatives of Nile blue, and rhodamines such as Rhodamine 123.

Examples of formulations containing a photosensitising compound as an active compound, PVA, cross-linker and modulator are shown below.

| Formulation (1) | Formulation (2) |
| --- | --- |
| 20% w/w PVA | 22% w/w PVA |
| 2.5% w/w Borax | 2.3% w/w Borax |
| 0.5% w/w Methylene Blue | 0.2% w/w Meso-tetra (N-methyl-4-pyridyl) porphine tetra tosylate |
| 0.5% w/w D-mannitol | 1.5% w/w D-mannitol |
| Up to 100 g with deionised water | Up to 100 g with deionised water |

The gel may be used for the topical application of drug substances to the following areas of the body for the purposes of achieving any or all of drug absorption to the systemic circulation, localised drug absorption into the underlying tissue structures, such as epithelial layers, dermis and epidermis, or localised drug absorption into a cavity or space associated with the anatomical structures mentioned below.

1. areas of intact skin, such as the skin on the hands and feet, toes, skin on the arms and legs, skin on the torso, skin on the face, lips, ears and neck
2. areas of intact skin and hair bearing skin on the genital areas, armpits, scalp and anal regions
3. acute lacerations and areas of trauma on skin, such as the skin on the hands and feet, skin on the arms and legs, skin on the torso, skin on the face, lips, ears, ear canal and neck
4. acute lacerations and areas of trauma areas on skin and hair bearing skin on the genital areas, armpits, scalp and anal regions
5. to mucous membranes, both normal and those suffering some form of chronic or acute trauma, in the nose, nasal cavities, mouth, buccal membranes, tongue, oropharynx, soft palate and rectum
6. to mucous membranes, both normal and those suffering some form of chronic or acute trauma, in the lower and upper female reproductive tracts, to include vulva, vaginal walls and cervix
7. to mucous membranes, both normal and those suffering some form of chronic or acute trauma, in the male reproductive tract, to include all parts of the penis
8. to mucous membranes, both normal and those suffering some form of chronic or acute trauma, found on the eye, conjunctiva and eye lids
9. keratinised structures, such as the finger nails, toe nails, cuticles and surrounding skin.

ANNEX 1
The following active pharmaceutical substances may be added to the semi-solid
Drugs that are used to treat disorders of the gastro-intestinal system
Examples include but are not necessarily limited to atropine sulphate, dicycloverine hydrochloride (dicyclomine hydrochloride), propantheline bromide and hyoscine butylbromide, Alverine, mebeverine, and peppermint oil, Metoclopramide and domperidone, Cimetidine, famotidine, nizatidine, ranitidine, pirenzepine, tripotassium dicitratobismuthate, sucralfate, misoprostol, esomeprazole, lansoprazole, omeprazole, pantoprazole, triamterene, co-amilofruse, triamterene with furosemide, spironolactone, adenosine, amiodarone hydrochloride, disopyramide, flecainide acetate, procainamide hydrochloride, propafenone hydrochloride, lidocaine hydrochloride, mexiletine hydrochloride, acebutolol, atenolol, bisoprolol fumarate, carvedilol, celiprolol hydrochloride, esmolol hydrochloride, labetalol hydrochloride, metoprolol tartrate, nadolol, nebivolol, oxprenolol hydrochloride, pindolol, sotalol hydrochloride, timolol maleate, bosentan, diazoxide, hydralazine hydrochloride, iloprost, minoxidil, sildenafil, sitaxentan sodium, sodium nitroprusside, clonidine hydrochloride, cilostazol, inositol nicotinate, moxisylyte, naftidrofuryl oxalate, pentoxifylline, dobutamine, dopamine hydrochloride, dopexamine hydrochloride, ephedrine hydrochloride, metaraminol, noradrenaline acid tartrate/norepinephrine bitartrate, phenylephrine hydrochloride, adrenaline/epinephrine, heparin, low molecular weight heparins, heparinoids, hirudins, fondaparinux, warfarin sodium, acenocoumarol, phenindione, protamine sulphate, abciximab, aspirin, clopidogrel, dipyridamole, eptifibatide, tirofiban, alteplase, reteplase, streptokinase, tenecteplase, urokinase, etamsylate, tranexamic acid, colesevelam hydrochloride, rabeprazole sodium, balsalazide sodium, mesalazine, olsalazine sodium, sulfasalazine, beclometasone dipropionate, budesonide, hydrocortisone, prednisolone, adalimumab, infliximab, sodium cromoglicate, ursodeoxycholic acid, colestyramine, aprotinin, pancreatin
Drugs that are used to treat disorders of the cardiovascular system, such as
digoxin, digitoxin, enoximone, bendroflumethiazide, chlortalidone, cyclopenthiazide, indapamide, metolazone, xipamide, furosemide, bumetanide, torasemide, amiloride hydrochloride, beclometasone dipropionate, budesonide, ciclesonide, fluticasone propionate, mometasone furoate, sodium cromoglicate, nedocromil sodium, montelukast, zafirlukast, cetirizine hydrochloride, desloratadine, fexofenadine hydrochloride, levocetirizine hydrochloride, loratadine, mizolastine, alimemazine tartrate, chlorphenamine maleate, clemastine, cyproheptadine hydrochloride, hydroxyzine hydrochloride, ketotifen, promethazine hydrochloride, omalizumab, adrenaline/epinephrine, doxapram hydrochloride, beractant, poractant alfa, carbocisteine, erdosteine, mecysteine hydrochloride, menthol, eucalyptus, codeine phosphate, pholcodine, pseudoephedrine hydrochloride.
Drugs that are used to treat disorders of the Central nervous system, such as
Nitrazepam, flurazepam, loprazolam, lormetazepam, temazepam, zaleplon, zolpidem tartrate, zopiclone, chloral hydrate, triclofos sodium, clomethiazole, promethazine hydrochloride, sodium oxybate, clomethiazole, buspirone, meprobamate, barbiturates, benperidol, chlorpromazine methyldopa, moxonidine, guanethidine monosulphate, doxazosin, indoramin, prazosin, terazosin, cilazapril, enalapril maleate, fosinopril sodium, imidapril hydrochloride, lisinopril, moexipril hydrochloride, perindopril, erbumine, quinapril, ramipril, trandolapril, candesartan cilexetil, eprosartan, irbesartan, losartan potassium, olmesartan, medoxomil, telmisartan, valsartan, aliskiren, glyceryl trinitrate, isosorbide dinitrate, isosorbide mononitrate, amlodipine, diltiazem hydrochloride, felodipine, isradipine, lacidipine, lercanidipine hydrochloride, nicardipine hydrochloride, nifedipine, nimodipine, nisoldipine, verapamil hydrochloride, ivabradine, nicorandil, zuclopenthixol acetate, zuclopenthixol, flupentixol decanoate, fluphenazine decanoate, haloperidol, pipotiazine palmitate, risperidone, zuclopenthixol decanoate, carbamazepine, valproic acid, lithium, amitriptyline hydrochloride, clomipramine hydrochloride, dosulepin hydrochloride, doxepin, imipramine hydrochloride, lofepramine, nortriptyline, trimipramine, mianserin hydrochloride, trazodone hydrochloride, phenelzine, isocarboxazid, tranylcypromine, citalopram, escitalopram, fluoxetine, fluvoxamine maleate, paroxetine, sertraline, duloxetine, flupentixol, mirtazapine, reboxetine, tryptophan, venlafaxine, atomoxetine, dexamfetamine sulphate, methylphenidate hydrochloride, modafinil, cocaine, orlistat, rimonabant, sibutramine hydrochloride, cinnarizine, cyclizine, promethazine hydrochloride, promethazine teoclate, chlorpromazine hydrochloride, perphenazine, prochlorperazine, trifluoperazine, domperidone, metoclopramide hydrochloride, dolasetron mesilate, granisetron, colestyramine, colestipol hydrochloride, ezetimibe, bezafibrate, ciprofibrate, fenofibrate, gemfibrozil, atorvastatin, fluvastatin, pravastatin sodium, rosuvastatin, simvastatin, acipimox, nicotinic acid, omega-3-acid ethyl esters, omega-3-marine triglycerides, ethanolamine oleate, ethanolamine oleate, sodium tetradecyl sulphate.
Drugs that are used to treat disorders of the Respiratory system, such as
bambuterol hydrochloride, fenoterol hydrobromide, formoterol fumarate, salbutamol, salmeterol, terbutaline sulphate, ephedrine hydrochloride, orciprenaline sulphate, ipratropium bromide, tiotropium, theophylline, aminophylline, dihydrocodeine tartrate, dipipanone hydrochloride, fentanyl, hydromorphone hydrochloride, meptazinol, methadone hydrochloride, morphine salts, oxycodone hydrochloride, papaveretum, pentazocine, pethidine hydrochloride, tramadol hydrochloride, tolfenamic acid, ergot alkaloids, pizotifen, clonidine hydrochloride, methysergide, carbamazepine, oxcarbazepine, ethosuximide, gabapentin, pregabalin, lamotrigine, levetiracetam, phenobarbital and other barbiturates, phenytoin, rufinamide, tiagabine, topiramate, valproate, vigabatrin, zonisamide, fosphenytoin sodium, lorazepam, midazolam, paraldehyde, phenobarbital sodium, phenytoin sodium, apomorphine hydrochloride, bromocriptine, cabergoline, pergolide, pramipexole, ropinirole, rotigotine, levodopa, co-beneldopa, co-careldopa, rasagiline, selegiline hydrochloride, entacapone, tolcapone, amantadine hydrochloride, benzatropine mesilate, benzatropine mesilate, orphenadrine hydrochloride, hydrochloride, flupentixol, haloperidol, levomepromazine, pericyazine, perphenazine, pimozide, prochlorperazine, promazine hydrochloride, sulpiride, trifluoperazine, hydrochloride, methadone hydrochloride, naltrexone hydrochloride, donepezil hydrochloride, galantamine, memantine hydrochloride, rivastigmine.

Drugs that are used to treat infections, such as
BENZYLPENICILLIN,
PHENOXYMETHYLPENICILLIN,
FLUCLOXACILLIN,
TEMOCILLIN
AMOXICILLIN,
AMPICILLIN, CO-AMOXICLAV, CO-FLUAMPICIL,
PIPERACILLIN,
TICARCILLIN
PIVMECILLINAM
HYDROCHLORIDE,
CEFACLOR,
CEFADROXIL,
CEFALEXIN, CEFIXIME,
CEFOTAXIME,
CEFPODOXIME,
CEFRADINE,
CEFTAZIDIME,
CEFTRIAXONE,
CEFUROXIME,
AZTREONAM,
ERTAPENEM,
IMIPENEM,
MEROPENEM,
TETRACYCLINE,
DEMECLOCYCLINE HYDROCHLORIDE,
DOXYCYCLINE,
LYMECYCLINE,
MINOCYCLINE,
OXYTETRACYCLINE
GENTAMICIN,
AMIKACIN, NEOMYCIN SULPHATE,
TOBRAMYCIN,
ERYTHROMYCIN,
AZITHROMYCIN,
CLARITHROMYCIN,
TELITHROMYCIN,
CLINDAMYCIN,
CHLORAMPHENICOL
SODIUM FUSIDATE,
VANCOMYCIN,
TEICOPLANIN,
DAPTOMYCIN,
LINEZOLID,
QUINUPRISTIN
LIOTHYRONINE
SODIUM
CARBIMAZOLE
IODINE AND IODIDE
PROPYLTHIOURACIL
FLUDROCORTISONE
ACETATE
BETAMETHASONE
CORTISONE ACETATE
DEFLAZACORT
DEXAMETHASONE
HYDROCORTISONE
METHYLPREDNISOLONE
ondansetron, palonosetron, tropisetron, aprepitant, nabilone, hyoscine hydrobromide, betahistine dihydrochloride, aspirin, paracetamol, nefopam hydrochloride, buprenorphine, codeine phosphate, diamorphine hydrochloride,
COLISTIN, CO-TRIMOXAZOLE,
SULFADIAZINE,
TRIMETHOPRIM,
CAPREOMYCIN,
CYCLOSERINE,
ETHAMBUTOL
HYDROCHLORIDE,
ISONIAZID,
PYRAZINAMIDE,
RIFABUTIN,
RIFAMPICIN,
STREPTOMYCIN,
DAPSONE,
CLOFAZIMINE,
METRONIDAZOLE,
TINIDAZOLE
CIPROFLOXACIN,
LEVOFLOXACIN,
MOXIFLOXACIN,
NALIDIXIC ACID,
NORFLOXACIN,
OFLOXACIN,
NITROFURANTOIN,
METHENAMINE
HIPPURATE,
AMPHOTERICIN,
ANIDULAFUNGIN,
CASPOFUNGIN,
FLUCONAZOLE,
FLUCYTOSINE,
GRISEOFULVIN,
ITRACONAZOLE,
KETOCONAZOLE,
NYSTATIN,
POSACONAZOLE,
TERBINAFINE,
VORICONAZOLE,
ABACAVIR,
DIDANOSINE,
EMTRICITABINE,
LAMIVUDINE,
STAVUDINE
TENOFOVIR
DISOPROXIL,
ZIDOVUDINE,
AMPRENAVIR,
ATAZANAVIR,
DARUNAVIR,
FOSAMPRENAVIR,
INDINAVIR, LOPINAVIR,
NELFINAVIR,
RITONAVIR,
SAQUINAVIR,
TIPRANAVIR,
EFAVIRENZ,
NEVIRAPINE,
ENFUVIRTIDE,
MARAVIROC,
ACICLOVIR,
DISODIUM
ETIDRONATE
DISODIUM
PAMIDRONATE
IBANDRONIC ACID
RISEDRONATE
SODIUM
SODIUM CLODRONATE
procyclidine hydrochloride, trihexyphenidyl hydrochloride, haloperidol, piracetam, riluzole, tetrabenazine, acamprosate calcium, disulfiram, bupropion hydrochloride, nicotine, varenicline, buprenorphine, lofexidine
FAMCICLOVIR,
INOSINE PRANOBEX,
VALACICLOVIR,
CIDOFOVIR,
GANCICLOVIR,
FOSCARNET SODIUM,
VALGANCICLOVIR,
ADEFOVIR DIPIVOXIL,
ENTECAVIR,
TELBIVUDINE,
AMANTADINE
HYDROCHLORIDE,
OSELTAMIVIR,
ZANAMIVIR,
PALIVIZUMAB,
RIBAVIRIN
ARTEMETHER WITH
LUMEFANTRINE,
CHLOROQUINE
MEFLOQUINE
PRIMAQUINE
PROGUANIL
HYDROCHLORIDE
PYRIMETHAMINE
QUININE
DOXYCYCLINE
DILOXANIDE FUROATE
METRONIDAZOLE
TINIDAZOLE
MEPACRINE
HYDROCHLORIDE
ATOVAQUONE
PENTAMIDINE
ISETIONATE
MEBENDAZOLE
PIPERAZINE Drugs that are used to treat disorders of the Endocrine system Such as
Insulins
CHLORPROPAMIDE
GLIBENCLAMIDE
GLICLAZIDE
GLIMEPIRIDE
GLIPIZIDE
TOLBUTAMIDE
METFORMIN
HYDROCHLORIDE
ACARBOSE
EXENATIDE
NATEGLINIDE
PIOGLITAZONE
REPAGLINIDE
ROSIGLITAZONE
SITAGLIPTIN
GLUCAGON
LEVOTHYROXINE
SODIUM
FLAVOXATE
HYDROCHLORIDE
OXYBUTYNIN
HYDROCHLORIDE
PROPANTHELINE
BROMIDE
PROPIVERINE
HYDROCHLORIDE
SOLIFENACIN PREDNISOLONE
TRIAMCINOLONE
OESTROGENS
TIBOLONE
ETHINYLESTRADIOL
RALOXIFENE
HYDROCHLORIDE
DYDROGESTERONE
MEDROXYPROGESTERONE
ACETATE
NORETHISTERONE
PROGESTERONE
TESTOSTERONE AND
ESTERS
MESTEROLONE
CYPROTERONE
ACETATE
DUTASTERIDE
FINASTERIDE
NANDROLONE
CLOMIFENE CITRATE
TETRACOSACTIDE
CHORIONIC
GONADOTROPHIN
CHORIOGONADOTROPIN
ALFA
FOLLITROPIN ALFA and
BETA
HUMAN MENOPAUSAL
GONADOTROPHINS
LUTROPIN ALFA
SOMATROPIN
PEGVISOMANT
THYROTROPIN ALFA
GONADORELIN
PROTIRELIN
VASOPRESSIN
DESMOPRESSIN
TERLIPRESSIN
CALCITONIN
(SALMON)/SALCATONIN
PARATHYROID
HORMONE
TERIPARATIDE
ALENDRONIC ACID
CYTARABINE
FLUDARABINE
PHOSPHATE
FLUOROURACIL
GEMCITABINE
MERCAPTOPURINE
METHOTREXATE
NELARABINE
PEMETREXED
RALTITREXED
TEGAFUR WITH
URACIL
TIOGUANINE
ETOPOSIDE
VINBLASTINE
SULPHATE
VINCRISTINE
SULPHATE
VINDESINE SULPHATE
VINORELBINE
AMSACRINE
ARSENIC TRIOXIDE
BEVACIZUMAB
BEXAROTENE
BORTEZOMIB
CETUXIMAB
CRISANTASPASE
DACARBAZINE
TEMOZOLOMIDE
HYDROXYCARBAMIDE
MITOTANE
PENTOSTATIN
CARBOPLATIN
CISPLATIN TILUDRONIC ACID
ZOLEDRONIC ACID
STRONTIUM
RANELATE
BROMOCRIPTINE
CABERGOLINE
QUINAGOLIDE
CETRORELIX
DANAZOL
GANIRELIX
GESTRINONE
METYRAPONE
TRILOSTANE
MECASERMIN
Drugs that are used to
treat conditions related to
obstetrics, gynaecology,
and urinary-tract
disorders, such as
7 Obstetrics,
gynaecology, and
urinary-tract disorders
CARBETOCIN
CARBOPROST
DINOPROSTONE
ERGOMETRINE
MALEATE
GEMEPROST
OXYTOCIN
ALPROSTADIL
INDOMETACIN
MIFEPRISTONE
ATOSIBAN
RITODRINE
HYDROCHLORIDE
SALBUTAMOL
TERBUTALINE
SULPHATE
ALFUZOSIN
HYDROCHLORIDE
DOXAZOSIN
INDORAMIN
PRAZOSIN
TAMSULOSIN
HYDROCHLORIDE
TERAZOSIN
BETHANECHOL
CHLORIDE
DISTIGMINE BROMIDE
DARIFENACIN
DULOXETINE
RITUXIMAB
INTERFERON ALFA
PEGINTERFERON ALFA
INTERFERON BETA
BACILLUS CALMETTE-
GUERIN
GLATIRAMER ACETATE
LENALIDOMIDE
NATALIZUMAB
DIETHYLSTILBESTROL
ETHINYLESTRADIOL
MEDROXYPROGESTER
ONE ACETATE
MEGESTROL ACETATE
NORETHISTERONE
ANASTROZOLE
EXEMESTANE
FULVESTRANT
LETROZOLE
TAMOXIFEN
TOREMIFENE
BICALUTAMIDE
BUSERELIN
CYPROTERONE
ACETATE
FLUTAMIDE
GOSERELIN
LEUPRORELIN SUCCINATE
TOLTERODINE
TARTRATE
TROSPIUM CHLORIDE
POTASSIUM CITRATE
SODIUM
BICARBONATE
SODIUM CITRATE
SODIUM CITRATE
GLYCINE
ALPROSTADIL
SILDENAFIL
TADALAFIL
VARDENAFIL
Drugs that are used in
the management of
malignant disease and
immunosuppression
Such as
DEXRAZOXANE
CALCIUM FOLINATE
CALCIUM
LEVOFOLINATE
DISODIUM FOLINATE
PALIFERMIN
MESNA
BUSULFAN
CARMUSTINE
CHLORAMBUCIL
CYCLOPHOSPHAMIDE
ESTRAMUSTINE
PHOSPHATE
IFOSFAMIDE
LOMUSTINE
MELPHALAN
THIOTEPA
TREOSULFAN
BLEOMYCIN
DACTINOMYCIN
DAUNORUBICIN
DOXORUBICIN
HYDROCHLORIDE
EPIRUBICIN
HYDROCHLORIDE
IDARUBICIN
HYDROCHLORIDE
MITOMYCIN
MITOXANTRONE
CAPECITABINE
CLADRIBINE
CLOFARABINE
FILGRASTIM
LENOGRASTIM
PEGFILGRASTIM
POTASSIUM CHLORIDE
POLYSTYRENE
SULPHONATE RESINS
SODIUM CHLORIDE
SODIUM CHLORIDE
VITAMIN A
RIBOFLAVIN
THIAMINE
PYRIDOXINE
HYDROCHLORIDE
NICOTINAMIDE
ASCORBIC ACID
ERGOCALCIFEROL
ALFACALCIDOL
CALCITRIOL
COLECALCIFEROL
DIHYDROTACHYSTEROL
PARICALCITOL
ALPHA TOCOPHERYL
ACETATE
MENADIOL SODIUM
PHOSPHATE
PHYTOMENADIONE
PENICILLAMINE
TRIENTINE OXALIPLATIN
PORFIMER SODIUM
TEMOPORFIN
PROCARBAZINE
DASATINIB
ERLOTINIB
IMATINIB
SORAFENIB
SUNITINIB
DOCETAXEL
PACLITAXEL
IRINOTECAN
HYDROCHLORIDE
TOPOTECAN
TRABECTEDIN
TRASTUZUMAB
TRETINOIN
AZATHIOPRINE
MYCOPHENOLATE
MOFETIL
BASILIXIMAB
CICLOSPORIN
DACLIZUMAB
SIROLIMUS
TACROLIMUS
ALEMTUZUMAB
FLURBIPROFEN
IBUPROFEN
INDOMETACIN
KETOPROFEN
MEFENAMIC ACID
MELOXICAM
NABUMETONE
NAPROXEN
PIROXICAM
SULINDAC
TENOXICAM
TIAPROFENIC ACID
SODIUM
AUROTHIOMALATE
AURANOFIN
PENICILLAMINE
CHLOROQUINE
HYDROXYCHLOROQUINE
SULPHATE
AZATHIOPRINE
CICLOSPORIN
LEFLUNOMIDE
METHOTREXATE
SULFASALAZINE
COLCHICINE
ALLOPURINOL
PROBENECID
SULFINPYRAZONE
RASBURICASE
GLUCOSAMINE
NEOSTIGMINE
DISTIGMINE BROMIDE
EDROPHONIUM
CHLORIDE
PYRIDOSTIGMINE
BROMIDE
BACLOFEN
DANTROLENE SODIUM
DIAZEPAM
TIZANIDINE
HYALURONIDASE
Drugs that are used to
treat disorders of the eye
Such as
CHLORAMPHENICOL
CIPROFLOXACIN
FUSIDIC ACID
GENTAMICIN
LEVOFLOXACIN
NEOMYCIN SULPHATE
OFLOXACIN
POLYMYXIN B
SULPHATE
ACETATE
TRIPTORELIN
LANREOTIDE
OCTREOTIDE
Cytotoxic drugs
Drugs that are used to
treat disorders related to
nutrition and blood
ERROUS SULPHATE
FERROUS FUMARATE
FERROUS GLUCONATE
POLYSACCHARIDE-
IRON COMPLEX
SODIUM FEREDETATE
IRON DEXTRAN
IRON SUCROSE
HYDROXOCOBALAMIN
CYANOCOBALAMIN
FOLIC ACID
DARBEPOETIN ALFA
EPOETIN ALFA, BETA,
and DELTA
METHOXY
POLYETHYLENE
GLYCOL-EPOETIN
BETA
DEFERASIROX
DEFERIPRONE
DESFERRIOXAMINE
MESILATE
ECULIZUMAB
ANAGRELIDE
HYDROCORTISONE
ACETATE
PREDNISOLONE
RIMEXOLONE
ANTAZOLINE
SULPHATE
AZELASTINE
HYDROCHLORIDE
EMEDASTINE
EPINASTINE
HYDROCHLORIDE
KETOTIFEN
LODOXAMIDE
NEDOCROMIL SODIUM
OLOPATADINE
SODIUM
CROMOGLICATE
ATROPINE SULPHATE
CYCLOPENTOLATE
HYDROCHLORIDE
HOMATROPINE
HYDROBROMIDE
TROPICAMIDE
PHENYLEPHRINE
HYDROCHLORIDE
BETAXOLOL
HYDROCHLORIDE
CARTEOLOL
HYDROCHLORIDE
LEVOBUNOLOL
HYDROCHLORIDE
METIPRANOLOL
TIMOLOL MALEATE
BIMATOPROST
LATANOPROST
TRAVOPROST
BRIMONIDINE
TARTRATE
DIPIVEFRINE
HYDROCHLORIDE
ACETAZOLAMIDE
BRINZOLAMIDE
DORZOLAMIDE
PILOCARPINE
LIDOCAINE
HYDROCHLORIDE
OXYBUPROCAINE
DIHYDROCHLORIDE
ZINC ACETATE
CARNITINE
AGALSIDASE ALFA and
BETA
IMIGLUCERASE
MIGLUSTAT
LARONIDASE
IDURSULFASE
GALSULFASE
MERCAPTAMINE
NITISINONE
CARGLUMIC ACID
SODIUM
PHENYLBUTYRATE
HAEM ARGINATE
Drugs that are used to
treat disorders of the
musculoskeletal and joint
diseases
ACECLOFENAC
ACEMETACIN
AZAPROPAZONE
CELECOXIB
DEXIBUPROFEN
DEXKETOPROFEN
DICLOFENAC SODIUM
ETODOLAC
ETORICOXIB
FENBUFEN
FENOPROFEN
PARAFFIN, YELLOW,
SOFT
POLYVINYL ALCOHOL
POVIDONE
SODIUM CHLORIDE
ZINC SULPHATE
FLUORESCEIN SODIUM
ACETYLCHOLINE
CHLORIDE
APRACLONIDINE
DICLOFENAC SODIUM
FLURBIPROFEN
SODIUM
KETOROLAC
TROMETAMOL
PEGAPTANIB SODIUM
RANIBIZUMAB
VERTEPORFIN
Drugs that are used to
treat disorders of the ear,
nose, and oropharynx
Such as
ALUMINIUM ACETATE
AZELASTINE
HYDROCHLORIDE
BECLOMETASONE
DIPROPIONATE
BETAMETHASONE
SODIUM PHOSPHATE
BUDESONIDE
FLUNISOLIDE
FLUTICASONE
PROPIONATE
MOMETASONE
FUROATE
TRIAMCINOLONE
ACETONIDE
SODIUM
CROMOGLICATE
EPHEDRINE
HYDROCHLORIDE
XYLOMETAZOLINE
HYDROCHLORIDE
IPRATROPIUM
BROMIDE
BENZYDAMINE
HYDROCHLORIDE
CARMELLOSE SODIUM -continued

| | | |
|---|---|---|
| PROPAMIDINE | HYDROCHLORIDE | CORTICOSTEROIDS |
| ISETIONATE | PROXYMETACAINE | DOXYCYCLINE |
| ACICLOVIR | HYDROCHLORIDE | FLURBIPROFEN |
| BETAMETHASONE | TETRACAINE | LOCAL ANAESTHETICS |
| DEXAMETHASONE | HYDROCHLORIDE | SALICYLATES |
| FLUOROMETHOLONE | ACETYLCYSTEINE | AMPHOTERICIN |
| SODIUM CHLORIDE | CARBOMERS | MICONAZOLE |
| THYMOL | CARMELLOSE SODIUM | NYSTATIN |
| PILOCARPINE | HYDROXYETHYLCELLULOSE | CHLORHEXIDINE |
| HYDROCHLORIDE | HYPROMELLOSE | GLUCONATE |
| Drugs that are used to | LIQUID PARAFFIN | HEXETIDINE |
| treat disorders of the skin | SALICYLIC ACID | HYDROGEN PEROXIDE |
| Such as | CO-CYPRINDIOL | PHOTODYNAMIC |
| CALAMINE | ISOTRETINOIN | THERAPY |
| CROTAMITON | SALICYLIC ACID | Drugs that are used to |
| DOXEPIN | FORMALDEHYDE | induce anaesthesia, such |
| HYDROCHLORIDE | GLUTARALDEHYDE | as; |
| HYDROCORTISONE | SILVER NITRATE | THIOPENTAL SODIUM |
| HYDROCORTISONE | DICLOFENAC SODIUM | ETOMIDATE |
| BUTYRATE | FLUOROURACIL | KETAMINE |
| ALCLOMETASONE | EFLORNITHINE | PROPOFOL |
| DIPROPIONATE | FINASTERIDE | ATROPINE SULPHATE |
| BETAMETHASONE | MINOXIDIL | GLYCOPYRRONIUM |
| ESTERS | MUPIROCIN | BROMIDE |
| CLOBETASOL | NEOMYCIN SULPHATE | HYOSCINE |
| PROPIONATE | POLYMYXINS | HYDROBROMIDE |
| CLOBETASONE | SILVER SULFADIAZINE | DIAZEPAM |
| BUTYRATE | FUSIDIC ACID | LORAZEPAM |
| DIFLUCORTOLONE | METRONIDAZOLE | MIDAZOLAM |
| VALERATE | AMOROLFINE | TEMAZEPAM |
| FLUDROXYCORTIDE | BENZOIC ACID | KETOROLAC |
| FLUOCINOLONE | CLOTRIMAZOLE | TROMETAMOL |
| ACETONIDE | ECONAZOLE NITRATE | PARECOXIB |
| FLUOCINONIDE | GRISEOFULVIN | ALFENTANIL |
| FLUOCORTOLONE | KETOCONAZOLE | FENTANYL |
| FLUTICASONE | MICONAZOLE NITRATE | REMIFENTANIL |
| PROPIONATE | NYSTATIN | ATRACURIUM |
| MOMETASONE | SALICYLIC ACID | BESILATE |
| FUROATE | SULCONAZOLE | CISATRACURIUM |
| TRIAMCINOLONE | NITRATE | MIVACURIUM |
| ACETONIDE | TERBINAFINE | PANCURONIUM |
| ICHTHAMMOL | TIOCONAZOLE | BROMIDE |
| CALCIPOTRIOL | UNDECENOATES | ROCURONIUM |
| CALCITRIOL | ACICLOVIR | BROMIDE |
| TACALCITOL | PENCICLOVIR | VECURONIUM |
| TAZAROTENE | IDOXURIDINE IN | BROMIDE |
| TARS | DIMETHYL SULFOXIDE | SUXAMETHONIUM |
| DITHRANOL | BENZYL BENZOATE | CHLORIDE |
| SALICYLIC ACID | CARBARYL | EDROPHONIUM |
| ACITRETIN | DIMETICONE | CHLORIDE |
| CICLOSPORIN | MALATHION | NEOSTIGMINE |
| EFALIZUMAB | PERMETHRIN | METILSULFATE |
| METHOTREXATE | PHENOTHRIN | FLUMAZENIL |
| PIMECROLIMUS | ALCOHOL | NALOXONE |
| TACROLIMUS | SODIUM CHLORIDE | HYDROCHLORIDE |
| BENZOYL PEROXIDE | CHLORHEXIDINE | DANTROLENE SODIUM |
| AZELAIC ACID | CETRIMIDE | LIDOCAINE |
| ANTIBACTERIALS | POVIDONE-IODINE | HYDROCHLORIDE |
| ADAPALENE | TRICLOSAN | BUPIVACAINE |
| TRETINOIN | HYDROGEN PEROXIDE | HYDROCHLORIDE |
| ISOTRETINOIN | POTASSIUM | LEVOBUPIVACAINE |
| ABRASIVE AGENTS | PERMANGANATE | PRILOCAINE |
| CORTICOSTEROIDS | BECAPLERMIN | HYDROCHLORIDE |
| NICOTINAMIDE | ALUMINIUM SALTS | PROCAINE |
| | GLYCOPYRRONIUM | HYDROCHLORIDE |
| | BROMIDE | ROPIVACAINE |
| | PHOTOSENSITISERS | HYDROCHLORIDE |
| | USED IN | TETRACAINE |

REFERENCES

1. KUROKAWA H, SHIBAYAMA M, ISHIMARU T, NOMURA S, WU W I. Phase-behavior and sol-gel transition of poly(vinyl alcohol) borate complex in aqueous-solution. Polymer. 1992; 33(10):2182-2188.
2. SHIBAYAMA M, ADACHI M, IKKAI F, KUROKAWA H, SAKURAI S, NOMURA S. Gelation of poly(vinyl alcohol) vanadate aqueous-solutions. Macromolecules. 1993; 26(4):623-627.
3. Tsujimoto M, Shibayama M. Dynamic light scattering study on reentrant sol-gel transition of poly(vinyl alcohol)-congo red complex in aqueous media. Macromolecules. 2002; 35(4):1342-1347.
4. Eliseev A A, Lukashin A V, Vertegel A A, Heifets L I, Zhirov A I, Tretyakov Y D. Complexes of cu(II) with poly-vinyl alcohol as precursors for the preparation of CuO/SiO2 nanocomposites. Materials Research Innovations. 2000; 3(5):308-312.
5. BOWCHER T L, DAWBER J G. C-13 and B-11 nuclear magnetic-resonance study of the reaction of polyvinyl-alcohol) with the tetrahydroxyborate ion. Polymer Communications. 1989; 30(7):215-217.
6. DAWBER J G, GREEN S I E. An B-11 nuclear-magnetic-resonance study of the reaction of the tetrahydroxyborate ion with polyhydroxy compounds. Journal of the Chemical Society-Faraday Transactions i. 1986; 82:3407-3413.
7. Lin H L, Yu T L, Cheng C H. Reentrant behavior of poly(vinyl alcohol)-borax semidilute aqueous solutions. Colloid Polym Sci. 2000; 278(3):187-194.
8. Lin H L, Liu W H, Liu Y F, Cheng C H. Complexation equilibrium constants of poly(vinyl alcohol)-borax dilute aqueous solutions—consideration of electrostatic charge repulsion and free ions charge shielding effect. J Polym Res—Taiwan. 2002; 9(4):233-238.
9. PEZRON E, LEIBLER L, LAFUMA F. Complex-formation in polymer-ion solutions. 2. poly-electrolyte effects. Macromolecules. 1989; 22(6):2656-2662.
10. PEZRON E, LEIBLER L, RICARD A, LAFUMA F, AUDEBERT R. Complex-formation in polymer ion solutions. 1. polymer concentration effects. Macromolecules. 1989; 22(3):1169-1174.
11. PEZRON E, RICARD A, LAFUMA F, AUDEBERT R. Reversible gel formation induced by ion complexation. 1. borax galactomannan interactions. Macromolecules. 1988; 21(4):1121-1125.
12. Lin H L, Liu Y F, Yu T L, Liu W H, Rwei S P. Light scattering and viscoelasticity study of poly(vinyl alcohol)-borax aqueous solutions and gels. Polymer. 2005; 46(15): 5541-5549.
13. KOIKE A, NEMOTO N, INOUE T, OSAKI K. Dynamic light-scattering and dynamic viscoelasticity of poly(vinyl alcohol) in aqueous borax solutions. 1. concentration-effect. Macromolecules. 1995; 28(7):2339-2344.
14. Nemoto N, Koike A, Osaki K. Dynamic light scattering and dynamic viscoelasticity of poly(vinyl alcohol) in aqueous borax solutions. 2. polymer concentration and molecular weight effects. Macromolecules. 1996; 29(5):1445-1451.
15. Takada A, Nishimura P, Koike A, Nemoto N. Dynamic light scattering and dynamic viscoelasticity of poly(vinyl alcohol) in aqueous borax solutions. 4. further investigation on polymer concentration and molecular weight dependencies. Macromolecules. 1998; 31(2):436-443.
16. Koga K, Takada A, Nemoto N. Dynamic light scattering and dynamic viscoelasticity of poly(vinyl alcohol) in aqueous borax solutions. 5. temperature effects. Macromolecules. 1999; 32(26):8872-8879.
17. Lin H L, Liu W H, Shen K S, Yu T L, Cheng C H. Weak gel behaviour of poly(vinyl alcohol)-borax aqueous solutions. J Polym Res—Taiwan. 2003; 10(3):171-179.
18. Ide N, Sato T, Miyamoto T, Fukuda T. Thermoreversible hydrogel of short-chain O-(2,3-dihydroxypropyl)cellulose/borax aqueous solution. microscopic versus macroscopic properties. Macromolecules. 1998; 31(25):8878-8885.
19. PEZRON E, LEIBLER L, RICARD A, AUDEBERT R. Reversible gel formation induced by ion complexation. 2. phase-diagrams. Macromolecules. 1988; 21(4):1126-1131.
20. Ostergaard J, Larsen S W, Parshad H, Larsen C. Bupivacaine salts of diflunisal and other aromatic hydroxycarboxylic acids: Aqueous solubility and release characteristics from solutions and suspensions using a rotating dialysis cell model. European Journal of Pharmaceutical Sciences. 2005; 26(3-4):280-287.
21. Keita G, Ricard A. Continous swelling or collapse of chemically crosslinked gel of polyvinylalcohol by borate complexation. polymer bulletin. 1990; 24:627-632.
22. keita G, Ricard A, Audebert R, Perzon E, leibler L. The poly(vinyl alcohol)-borate system: Influence of polyelectrolyte effects on phase diagrams. polymer. 1995; 36(1): 49-54.
23. Higuchi T. Analysis of data on the medicament release from ointments. J Pharm Sci. 1962; 51:802-804.
24. Ricci E J, Lunardi L O, Nanclares D M A, Marchetti J M. Sustained release of lidocaine from poloxamer 407 gels. Int J. Pharm. 2005; 288(2):235-244.
25. PEPPAS NA. Analysis of fickian and non-fickian drug release from polymers. Pharm Acta Helv. 1985; 60(4):110-111.
26. Huang X, Chestang B L, Brazel C S. Minimization of initial burst in poly(vinyl alcohol) hydrogels by surface extraction and surface-preferential crosslinking. Int J Pharm. 2002; 248(1-2):183-192
27. Conner J M, Bulgrin V C. Equilibria between borate ion and some polyols in aqueous solution. Journal of inorganic nuclear chemistry 1967; 29:1953-1961.
28. Roy G L, Laferriere A L, Edwards J O. A comparative study of polyol complexes of arsenite, borate and tellurate ions. Journal of inorganic nuclear chemistry 1957; 4:106-114.
29. Penn S G, Hu H, Brown H, Lebrilla B. direct analysis of sugar alcohol borate complexes in plant extracts by matrix-assisted laser desorption/ionization fourier transform mass spectrometry. Anal. Chem. 1997; 69(1):2471-2477.
30. Jones, D. S., Woolfson, A. D. & Djokic, J. 1996, "Texture profile analysis of bioadhesive polymeric semisolids: mechanical characterization and investigation of interactions between formulation components", *J Appl Polym Sci*, vol. 61, pp. 2229-2234.
31. Punnia, M. A. 1987, "Evaluation of pH changes in inflammation of the subcutaneous air pouch lining in the rat, induced by carrageenan, dextran and *staphylococcus*", *Journal of oral pathology and medicine*, vol. 16, no. 1, pp. 36-44.
32. Anderson, A. B.; Colecchi, C.; Baronoski, R.; DeWitt, T. G. Local anesthesia in pediatric patients: Topical TAC versus Lidocaine. Aannals of emergency medicine 1990, 19, 519-522.
33. Hegenbarth, M. A.; Altieri, M. F.; Hawk, W. H. Comparison of topical tetracaine, adrenaline, and cocaine anesthesia with lidocaine infiltration for repair of lacerations in children Annals of emergency medicine 1990 19 63-67.

34. Singer, A. J.; Stark, M. J. LET versus EMLA for pretreating lacerations: a randomized trial Academic Emergency Medicine 2001 8 223-230.

What we claim is:

1. A gel formulation for use in filling a wound cavity and delivering an active ingredient thereto, having a pH range of 6.5 to 7.5, low bioadhesive strength and cohesive integrity and being formed from poly(vinyl) alcohol (PVA) polymer, a cross-linker being a salt form of boron that produces borate ions in aqueous solution, at least one compound which has a beneficial effect as an active ingredient in the wound and at least one modulator, the modulator being a low molecular weight species that is capable of binding borate or PVA in aqueous solution through a mono-diol or di-diol formation and reduces the pH of PVA-borate hydrogels;

wherein the modulator includes at least one compound chosen from the group consisting of mannitol, maltitol, dulcitol, D-sorbitol, xylitol, and meso-erythritol, and the amount of modulator is from 0.1 to 5.0% by weight based on the total weight of the formulation; and wherein the active ingredient is lidocaine hydrochloride and wherein the amount of lidocaine hydrochloride is 3% w/w or greater based on the total weight of the formulation.

2. A gel formulation as claimed in claim 1 wherein the poly(vinyl) alcohol has a molecular weight from 15,000 to 50,000.

3. A gel formulation as claimed in claim 1 having a degree of hydrolysis of from 75 to 99%.

4. A gel formulation as claimed in claim 1 wherein the amount of borate used is from 1.5 to 4% weight based on the total weight of the formulation.

5. A gel formulation as claimed in claim 1 wherein the amount of modulator added in the preparation of the gel is from 0.5 to 2% by weight based on the total weight of the formulation.

6. A gel formulation as claimed in claim 1 further comprising a support.

7. A gel formulation as claimed in claim 1, wherein the poly(vinyl) alcohol has a molecular weight from 20,000 to 40,000.

8. A gel formulation as claimed in claim 1 wherein the modulator is mannitol.

9. A gel formulation as claimed in claim 5 wherein the modulator is mannitol.

10. A gel formulation as claimed in claim 4 wherein the modulator is mannitol and the amount of modulator added in the preparation of the gel is from 0.5 to 2% by weight based on the total weight of the formulation.

* * * * *